United States Patent
Nishibayashi et al.

(10) Patent No.: US 8,251,059 B2
(45) Date of Patent: Aug. 28, 2012

(54) POWDER INHALER

(75) Inventors: Toru Nishibayashi, Tokushima (JP);
Shintaro Adachi, Tokushima (JP);
Tetsuya Sato, Tokushima (JP); Takaaki Nakao, Tokushima (JP)

(73) Assignees: Otsuka Pharmaceutical Co., Ltd., Tokyo (JP); Otsuka Techno Corporation, Naruto-Shi (JP)

( * ) Notice: Subject to any disclaimer, the term of this patent is extended or adjusted under 35 U.S.C. 154(b) by 730 days.

(21) Appl. No.: 12/305,273

(22) PCT Filed: Jun. 26, 2007

(86) PCT No.: PCT/JP2007/062746
§ 371 (c)(1),
(2), (4) Date: Dec. 17, 2008

(87) PCT Pub. No.: WO2008/001744
PCT Pub. Date: Jan. 3, 2008

(65) Prior Publication Data
US 2009/0205656 A1    Aug. 20, 2009

(30) Foreign Application Priority Data
Jun. 27, 2006  (JP) .................................. 2006-176630

(51) Int. Cl.
*A61M 15/00*  (2006.01)
*A61M 15/08*  (2006.01)
*A61M 16/00*  (2006.01)
*B05D 7/14*   (2006.01)
*B65D 83/06*  (2006.01)

(52) U.S. Cl. .......... 128/203.15; 128/203.19; 128/203.23

(58) Field of Classification Search ............. 128/200.16, 128/203.14, 203.15, 203.19, 203.22, 203.23, 128/203.24, 205.23; B05D 7/14; B65D 83/06; A61M 15/00, 16/00, 15/08
See application file for complete search history.

(56) References Cited

U.S. PATENT DOCUMENTS
5,033,463 A    7/1991  Cocozza .................. 128/203.21
(Continued)

FOREIGN PATENT DOCUMENTS
JP          3-184563         8/1991
(Continued)

OTHER PUBLICATIONS
International Search Report for International Application No. PCT/JP2007/062746 dated Sep. 5, 2007.
(Continued)

*Primary Examiner* — Oren Ginsberg
(74) *Attorney, Agent, or Firm* — Kratz, Quintos & Hanson, LLP

(57) ABSTRACT

The subject invention provides a powder inhaler enabling the user to complete powder drug inhalation with fewer steps, for improved user convenience.
A powder inhaler of the present invention comprises:
  a housing 1A having an admission port 2f on one end;
  a supplier having a drug-discharging hole, provided inside the housing 1A with a capacity sufficient to contain plural doses of a fine powder drug;
  a drug carrier having a measurement concave portion for receiving a single dose of a drug from the drug-discharging hole, the drug carrier being supported inside the housing 1A while being movable between a drug-receiving position for allowing drug supply from the drug-discharging hole to the measurement concave portion, and a drug-inhalation position for allowing drug inhalation from the measurement concave portion through the admission port;
  a cover cap C2 pivotably mounted to the housing 1A; and
  a vibrating means 60 brought into operation by pivoting the cover cap C2 so as to vibrate the supplier.

10 Claims, 42 Drawing Sheets

U.S. PATENT DOCUMENTS

| | | | | |
|---|---|---|---|---|
| 5,113,855 A * | 5/1992 | Newhouse | ............ | 128/203.12 |
| 5,201,308 A * | 4/1993 | Newhouse | ............ | 128/203.15 |
| 5,250,287 A | 10/1993 | Cocozza | ............ | 424/45 |
| 5,575,280 A | 11/1996 | Gupte et al. | ............ | 128/203.15 |
| 6,182,655 B1 | 2/2001 | Keller et al. | ............ | 128/203.15 |
| 6,655,380 B1 * | 12/2003 | Andersson et al. | ...... | 128/203.15 |
| 6,729,324 B2 | 5/2004 | Casper et al. | | |
| 7,107,988 B2 * | 9/2006 | Pinon et al. | ............ | 128/203.15 |
| 7,131,441 B1 * | 11/2006 | Keller et al. | ............ | 128/203.15 |
| 7,228,860 B2 * | 6/2007 | Andersson et al. | ...... | 128/203.15 |
| 7,387,122 B2 * | 6/2008 | Nishibayashi et al. | .. | 128/203.15 |
| 7,841,340 B2 * | 11/2010 | Andersson et al. | ...... | 128/203.15 |
| 2005/0103336 A1 | 5/2005 | Nishibayashi et al. | .. | 128/203.11 |
| 2009/0205657 A1 * | 8/2009 | Barney et al. | ............ | 128/203.15 |
| 2010/0242960 A1 * | 9/2010 | Zangerle | ............ | 128/203.15 |

FOREIGN PATENT DOCUMENTS

| | | |
|---|---|---|
| JP | 5-200115 | 8/1993 |
| JP | 6-502784 | 3/1994 |
| JP | 2005-501013 | 2/2000 |
| WO | WO 92/09322 A1 | 6/1992 |
| WO | WO 97/20589 A1 | 6/1997 |
| WO | WO 2004/033010 A1 | 4/2004 |

OTHER PUBLICATIONS

Taiwanese Office Action dated Jun. 7, 2011, issued for counterpart Taiwanese Patent Application No. 96123354, dated Jun. 7, 2011.

* cited by examiner (a)

(b)

(a)

(b)

(a)

(b)

(a)

(b)

(a)

(b)

(a)

(b)

(a)

(b)

POWDER INHALER

TECHNICAL FIELD

The present invention relates to a powder inhaler capable of administering multiple doses of a fine powder drug.

BACKGROUND ART

A known example of such a powder inhaler is one comprising: a housing having an admission port in its front area; a supplier for containing plural doses of a fine powder drug; a drug carrier for moving back and forth between the supplier and the admission port so as to supply a single dose of the fine powder drug from the supplier to the admission port; a detachable cover cap that covers the front area of the housing; and a bottom cap for operating the drug carrier, wherein the rear side of the housing has an opening, the bottom cap having a cap-like shape is formed to freely move back and forth while covering the back portion of the housing, the bottom cap and the drug carrier are connected by a connector penetrating through the opening, and, when the housing is covered by the cover cap, the back end of the cover and the front end of the bottom cap are met so that the cover cap enfolds the housing (see Patent Document 1).

The inhalation of the fine powder drug using the foregoing powder inhaler is performed by six operations as follows. As shown in FIG. 52, (1) the cover cap C2 is removed, and (2) the powder inhaler is held and shaken by hand so as to fill the drug carrier with the fine powder drug that is supplied from the supplier, (3) the bottom cap C1 is pushed to move the drug carrier from the drug-receiving position to the drug-inhalation position (the position enabling the user to inhale the drug from the admission port), (4) the user inhales the drug, (5) the bottom cap C1 is operated to move the drug carrier back to the drug-receiving position, and (6) the cover cap C2 is closed.

Patent Document 1: International Publication No. 2004/033010

DISCLOSURE OF THE INVENTION

Technical Problem

The foregoing known powder inhaler ensures a significantly high moisture-proof effect without having a dedicated moisture-proof casing; however, it requires the foregoing six steps for drug inhalation.

The present invention provides a powder inhaler enabling the user to complete powder drug inhalation in fewer steps, improving user convenience.

Technical Solution

A powder inhaler of the present invention comprises:
a housing having an admission port on one end;
a supplier having a drug-discharging hole, provided inside the housing with a capacity sufficient to contain plural doses of a fine powder drug;
a drug carrier having a measurement concave portion for receiving a single dose of a drug from the drug discharging hole, the drug carrier being supported inside the housing while being movable between a drug-receiving position for allowing drug supply from the drug-discharging hole to the measurement concave portion, and a drug-inhalation position for allowing drug inhalation from the measurement concave portion through the admission port;
a cover cap pivotably mounted to the housing;

at least one first engagement section mounted to the cover cap, and at least one second engagement section provided in a portion allowing the second engagement section to transmit vibration to the supplier, and that is engaged with the first engagement section by pivotably the cover cap and thereby vibrate the supplier.

In another embodiment, the first engagement section is provided on the inner side of the cover cap, and the second engagement section is provided on the housing.

In another embodiment, the first engagement section is provided on the inner side of the cover cap, and the second engagement section is provided on the external lateral face of the supplier.

In another embodiment, the powder inhaler further comprises:
an elastic member provided in the housing, to bias the drug carrier from the drug inhalation position to the drug-receiving position;
a lock mechanism for locking the drug carrier in the drug-inhalation position; and
a lock-releasing mechanism for unlocking the lock mechanism in response to a closing movement of the cover cap.

In another embodiment, the first engagement section is pivotably connected to the inner side of the cover cap, and the housing includes a guide member for pivoting the first engagement section while pivoting the cover cap, and guiding the first engagement section to the second engagement section. One modification of this powder inhaler further comprises:
an elastic member provided in the housing, to bias the drug carrier from the drug-inhalation position to the drug-receiving position;
a lock mechanism for locking the drug carrier in the drug-inhalation position; and
a lock-releasing mechanism for unlocking the lock mechanism in response to a closing movement of the cover cap,
wherein:
the lock-releasing mechanism includes a lock-releasing member, which is connected to the first engagement section and is guided by the guide section to a lock-releasing position.

In another embodiment, the second engagement section is mounted to a component incorporated in the housing, wherein the component can transmit vibration to the supplier.

A powder inhaler of the present invention comprises:
a housing having an admission port on one end;
a supplier having a drug-discharging hole, provided inside the housing with a capacity sufficient to contain plural doses of a fine powder drug;
a drug carrier having a measurement concave portion for receiving a single dose of a drug from the drug discharging hole, the drug carrier being supported inside the housing while being movable between a drug-receiving position for allowing drug supply from the drug-discharging hole to the measurement concave portion, and a drug-inhalation position for allowing drug inhalation from the measurement concave portion through the admission port;
a cover cap pivotably mounted to the housing; and
a vibrating means brought into operation by pivoting the cover cap so as to vibrate the supplier.

In one embodiment, the vibrating means includes at least one first engagement section mounted to the cover cap, and at least one second engagement section provided on the housing, and that is engaged with the first engagement section.

In another embodiment, the vibrating means includes at least one first engagement section mounted to the cover cap, and at least one second engagement section provided on the supplier, and that is engaged with the first engagement section.

EFFECT OF THE INVENTION

According to the present invention, when the cover cap is pivoted, the first engagement section is engaged with the second engagement section, thereby directly vibrating the supplier. As a result, the fine powder drug is supplied from the supplier to the measurement concave portion of the drug carrier. With this structure, in which the opening of the cover cap automatically vibrates the supplier, the user's action "(2) shake the powder inhaler by hand" in the foregoing known method can be omitted.

Furthermore, by providing an elastic member for biasing the drug carrier from the drug-inhalation position to the drug-receiving position; a lock mechanism for locking the drug carrier in the drug-inhalation position; and a lock-releasing mechanism for releasing the lock mechanism with the closing operation of the cover cap, the lock mechanism for locking the drug carrier in the drug inhalation position is unlocked in response to the closing of the cover cap, thereby causing the elastic member to return the drug carrier to the drug-receiving position. With this structure, the user's action "(5) operate the bottom cap to return the drug carrier to the drug-receiving position" in the foregoing known method can be omitted.

BRIEF DESCRIPTION OF DRAWINGS

FIG. 50(a) shows a cover cap opened, and FIG. 50(b) shows a cover cap closed.

Figure 1:
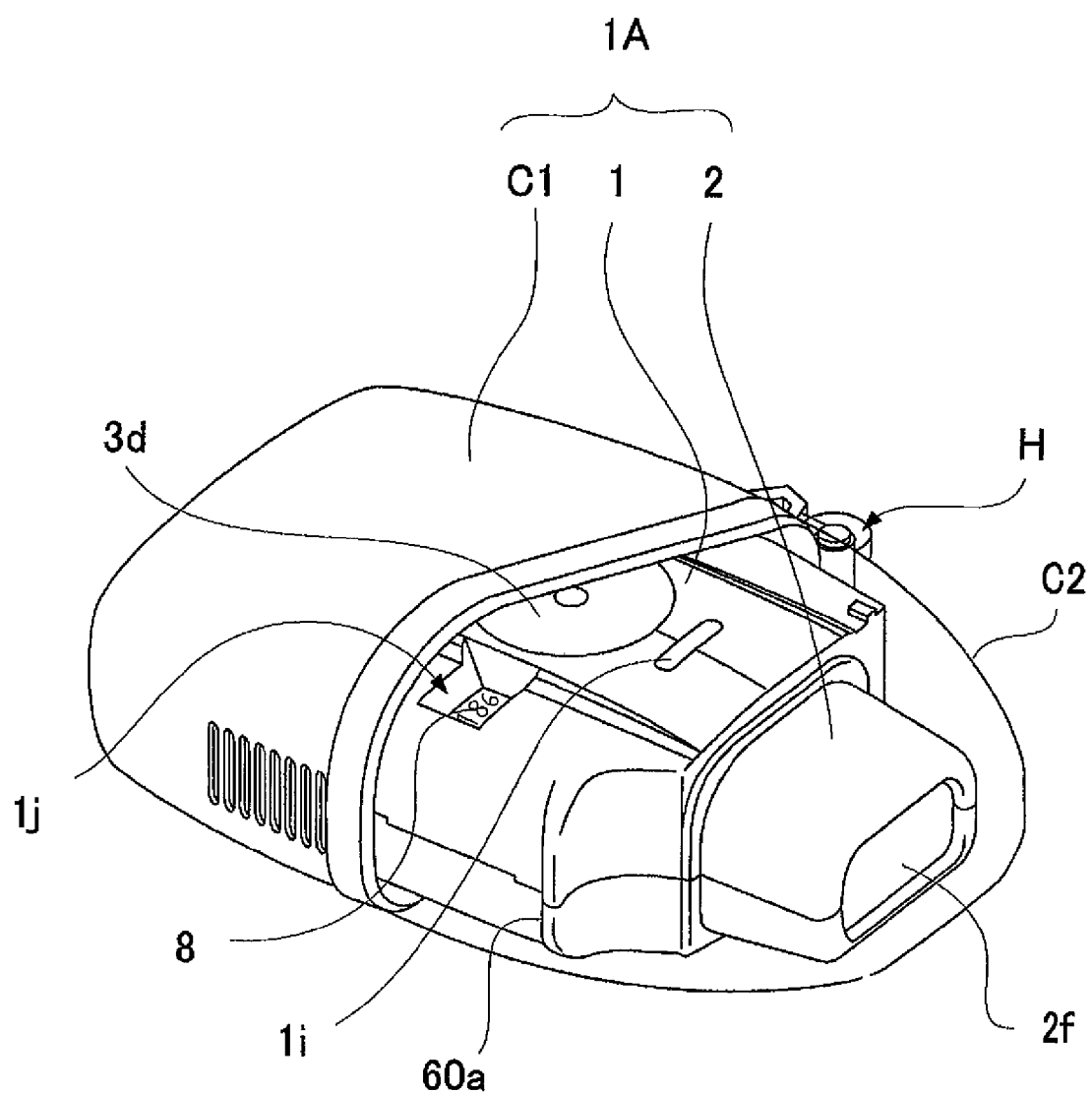
FIG. 1 is a perspective view of a powder inhaler according to the First Embodiment of the present invention.

REFERENCE NUMERALS 1A housing
1 housing body
C2 cover cap
2 mouthpiece
3 supplier
4 drug carrier
C1 bottom cap
60, 90, 100 vibrating means

BEST MODE FOR CARRYING OUT THE INVENTION

The following explains embodiments of the present invention with reference to Figures. Throughout the figures and embodiments, the same numerals are given to identical constituents.

Figure 2:
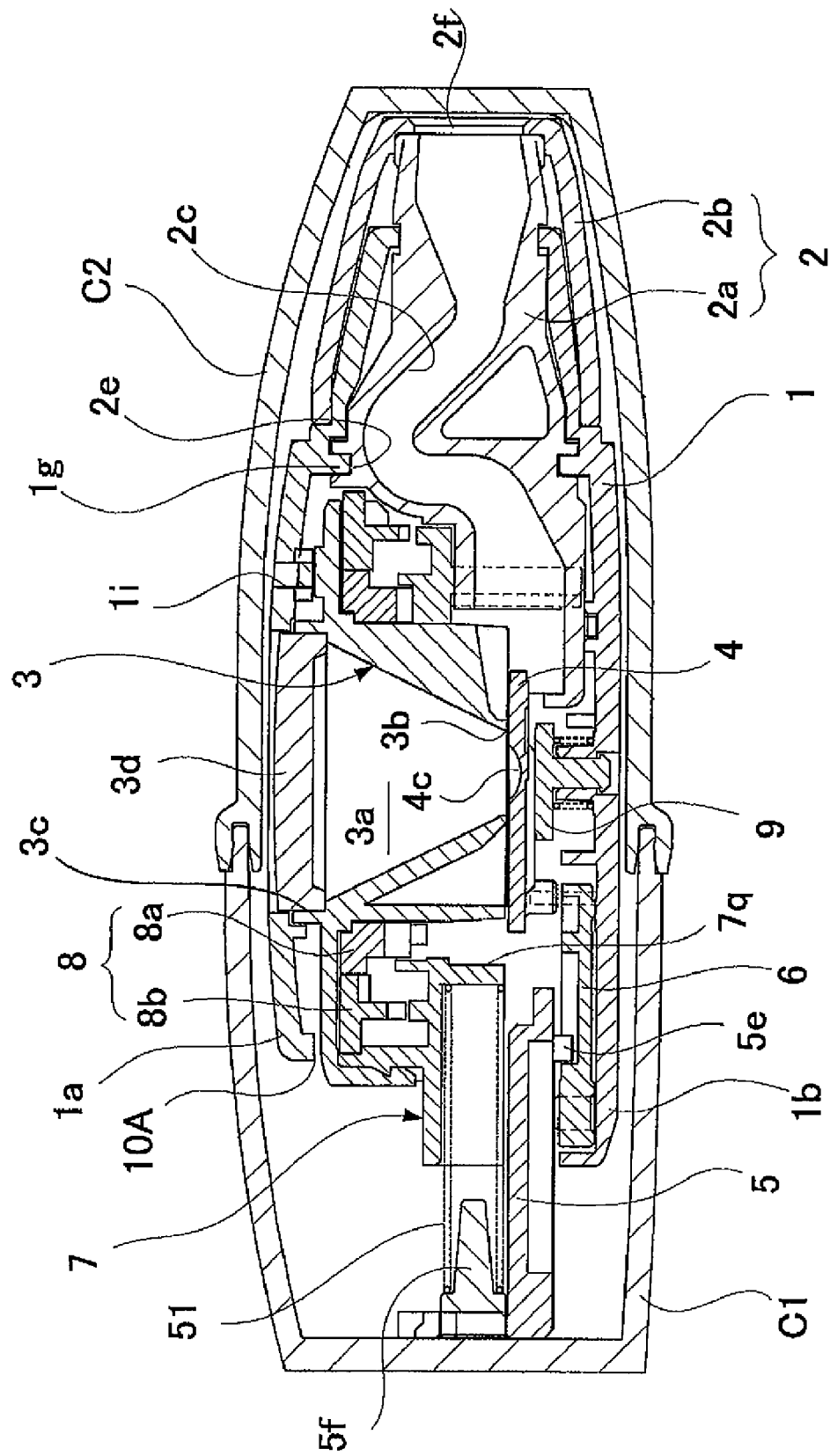
FIG. 2 is a vertical cross-sectional view of the powder inhaler.

The following explains the First Embodiment of the powder inhaler according to the present invention. FIG. 1 is a perspective view of the powder inhaler, and FIG. 2 is a vertical cross-sectional view of the powder inhaler. The powder inhaler is provided with a housing 1A including a housing body 1, a mouthpiece 2, and a bottom cap C1 for covering the back side of the housing body 1; a supplier 3 fixed to the housing body 1 and contains multiple doses of the fine powder drug; a drug carrier 4 for carrying a single dose of the fine powder drug supplied from the supplier 3; and a connector 5 for connecting the drug carrier 4 to the bottom cap C1; a locking member 6 for locking the bottom cap C1 via the connector 5; a cover cap C2 connected to the bottom cap C1 via a hinge H in an openable and closable manner; a base 7 for holding the supplier 3 inside the housing 1A; and a counter 8 rotatably supported between the supplier 3 and the base 7 and displays the number of doses. It is preferable that the cover cap C2 be formed of a transparent or translucent material and a bottom cap C1 be formed of an opaque material.

The powder inhaler includes a vibrating means 60 made of two separate parts formed respectively on the internal lateral face of the cover cap C2 and on the external lateral face of the housing 1A. When the cover cap C2 is pivotably opened, the parts of the vibrating means 60 are engaged, and thereby vibrate the housing 1A.

The vibrating means 60 is made of a first engagement section provided on the internal face the cover cap C2; and a second engagement section provided on the external lateral face of the housing body 1. The second engagement section is formed to be engageable with the first engagement section, and transfers the vibration to the supplier 3 through the housing body 1 when the cover cap C2 is pivoted.

Figure 23:
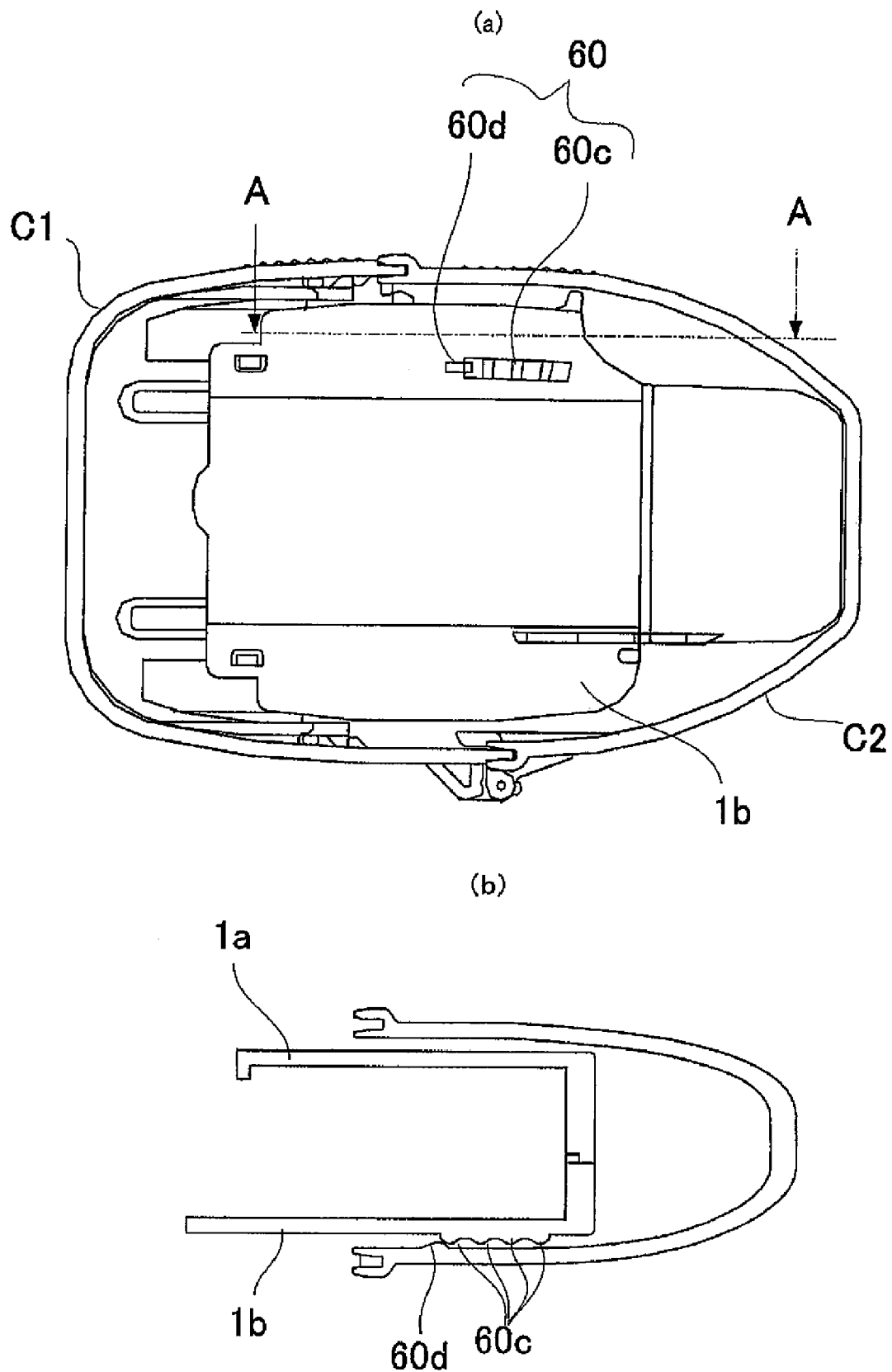
FIG. 23(a) is a bottom plan view of the inside of the powder inhaler, and 23(b) is a cross-sectional view of the main part, taken along the line A-A of 23(a).

The second engagement section is realized by a convex portion 60a formed on an external lateral face of the housing body 1. The first engagement section is realized by a plurality of concave portions 60b, which are arranged serially on the internal lateral face of the cover cap C2 to be engaged with the convex portion 60a. Further, as shown in FIG. 23, the second engagement section includes convex portions 60c formed on the external bottom face of the lower housing body 1b, and the first engagement section includes a convex portions 60d formed on the internal lateral face of the cover cap C2 to be engaged with the convex portion 60c. The convex portion 60c has a wavy cross-section as formed of a plurality of adjacent concave portions. The vibrating means 60 is not limited to the one in the figure, and may have a variety of shapes, such as a fin shape, a pectinate shape, etc.

As shown in FIG. 2, the housing body 1 includes an upper housing body 1a and a lower housing body 1b. The back end of the housing body 1 has an opening 10A through which the connector 5 is inserted.

Figure 10:
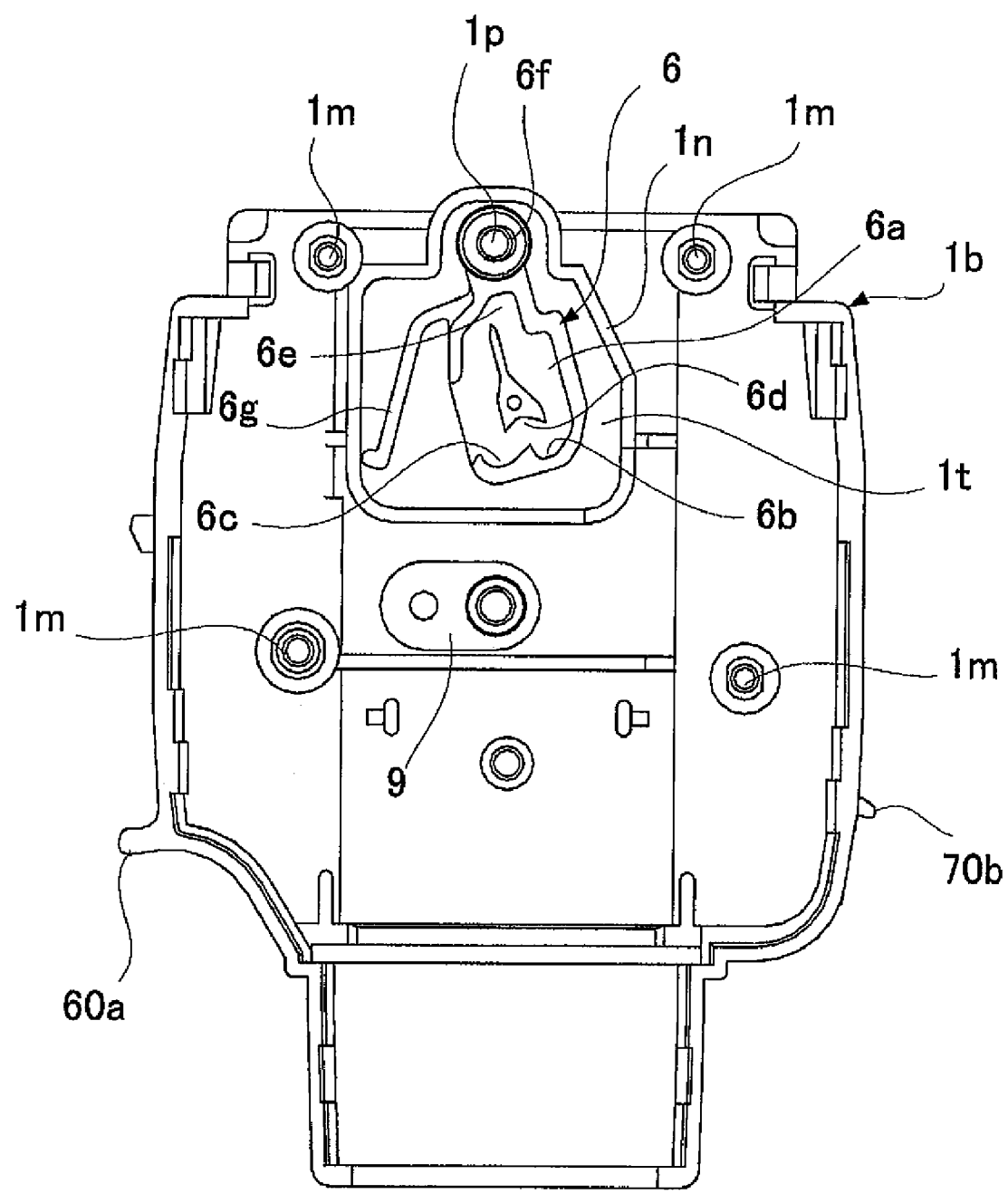
FIG. 10 is a plan view showing an order of assembly of the powder inhaler.
Figure 14:
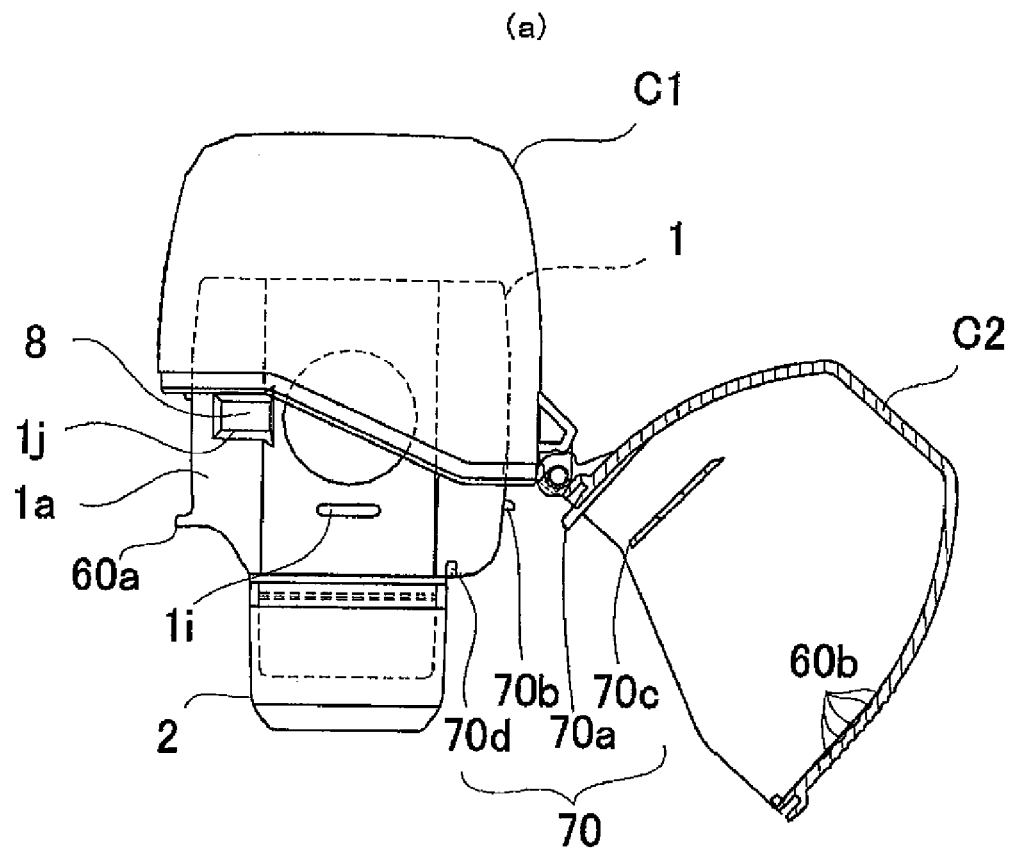
FIG. 14(a) is a plan view showing the powder inhaler before operation.
FIG. 14(b) is a plan view showing the powder inhaler after operation.
Figure 14:
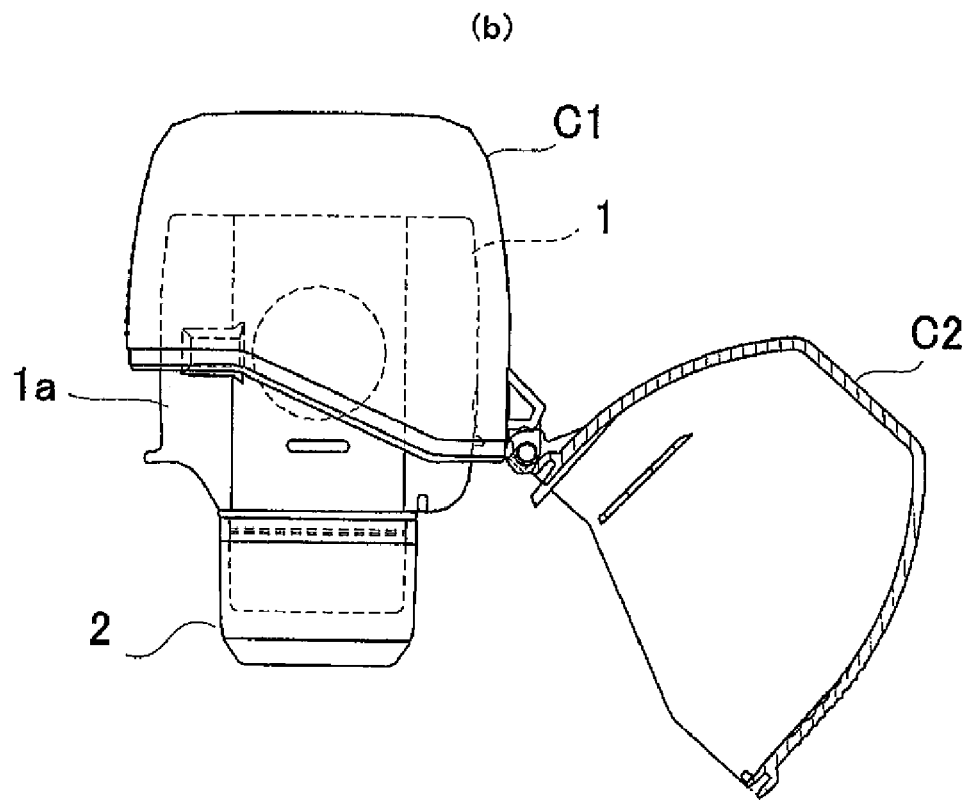

The upper housing body 1a and the lower housing body 1b are connected together in a snap-in manner with a latching pawl and a latching groove (both not shown). As shown in FIG. 1 and FIG. 14, an air inlet 1i in the form of a horizontal slit is provided in the front side of the upper housing body 1a, and a window 1j is provided in the portion where the counter 8 is provided so as to allow the user to read the display of the counter 8. As shown in FIG. 10, provided inside the lower housing body 1b are a guide axis 1m for guiding the connector 5, a storage 1t for storing the locking member 6 surrounded by a projecting portion in, and a pivot axis 1p of the locking member 6 formed in the storage 1t.

As shown in FIG. 2, the mouthpiece 2 is formed of a main body 2a and a cover 2b. The main body 2a is provided with a drug inhalation path 2c for dispersing a fine powder drug. Interdigitation grooves 2e are formed along the periphery of the main body 2a. The cover 2b is provided with an admission port 2f for allowing the user to intake the powder drug by his/her own inhalation action.

Figure 8:
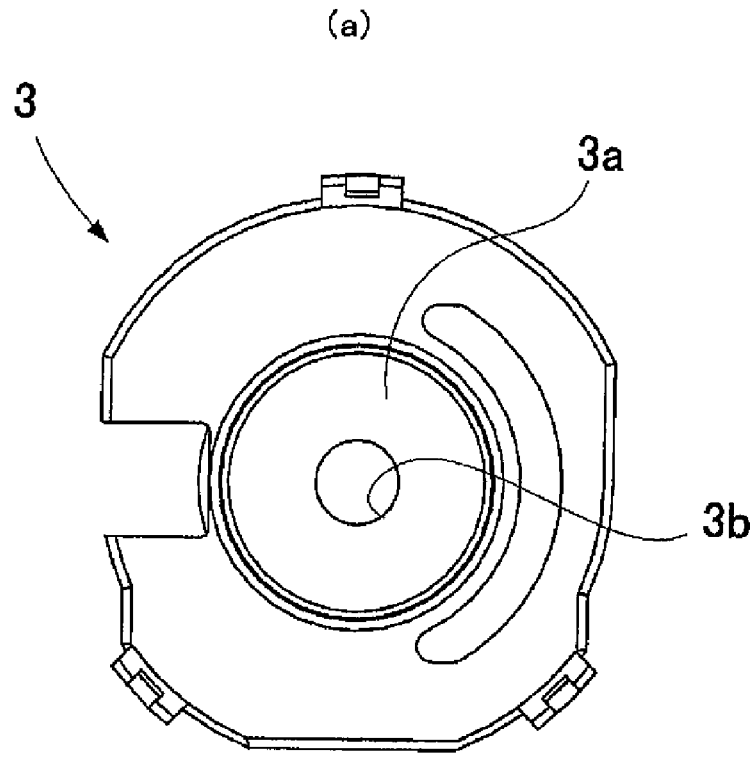
FIGS. 8(a) and 8(b) are a plan view and a bottom plan view, respectively, of a supplier of the powder inhaler.
Figure 8:
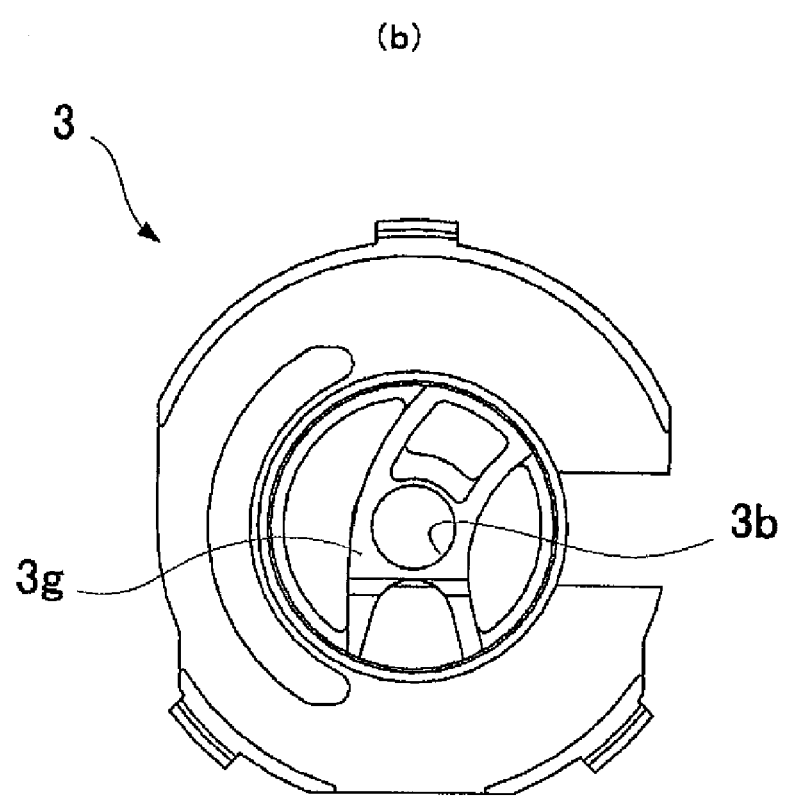
Figure 9:
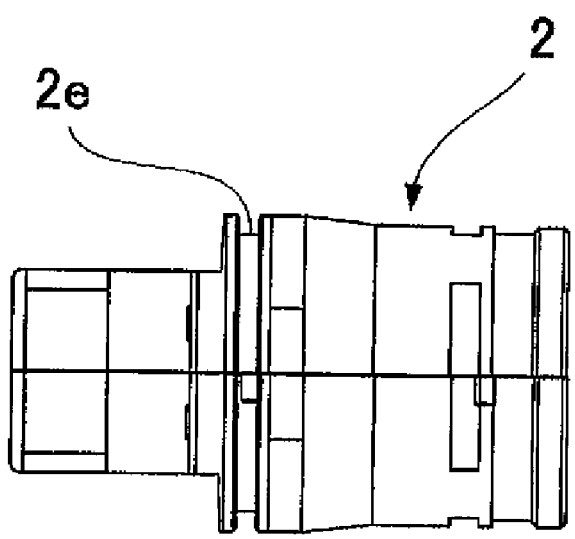
FIGS. 9(a) and 9(b) are a lateral view and a plan view, respectively, of a mouthpiece of the powder inhaler.
Figure 9:
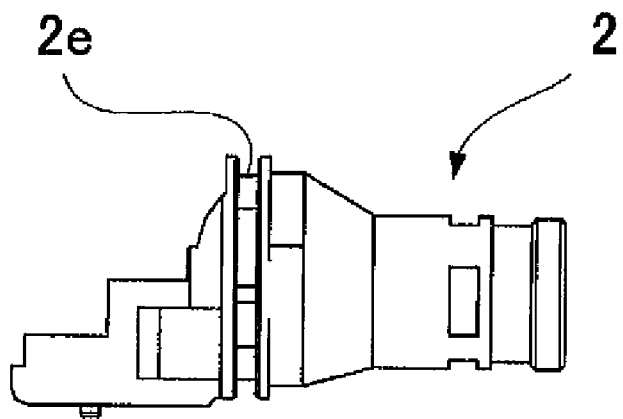

As shown in FIG. 2 and FIG. 8, the supplier 3 includes a funnelform hopper 3a for storing about 200 doses of the fine powder drug. A drug discharge outlet 3b is provided in the lower end of the hopper 3a. The upper end of the hopper 3a of the supplier 3 has an opening 3c covered with a lid 3d that protects the fine powder drug from humidity. The counter 8 is fitted to the exterior of the hopper 3a of the supplier 3. To decrease the contact area with the periphery of a measurement concave portion 4c (described later) of the drug carrier 4, a thick portion 3g is formed in the periphery of the drug discharge outlet 3b and in the portion corresponding to the sliding portion 4e (FIG. 5) of the drug carrier 4, so that the drug carrier 4 comes in contact only with the lower face of the thick portion 3g.

As shown in FIGS. 1 and 2, the cover cap C2 has sufficient size to cover the front area of the housing body 1 and the mouthpiece 2.

Figure 3:
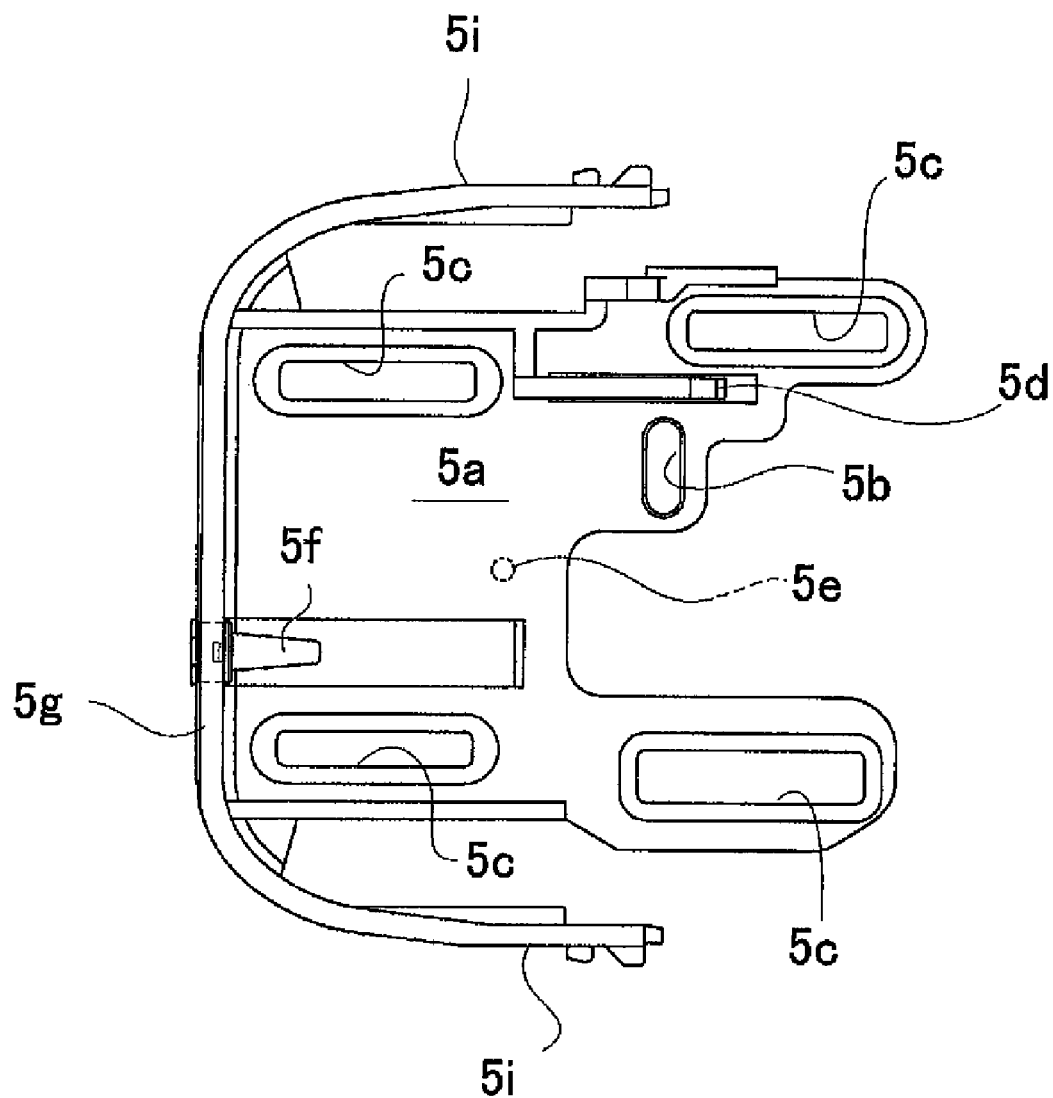
FIG. 3 is a plan view of a connector of the powder inhaler.
Figure 16:
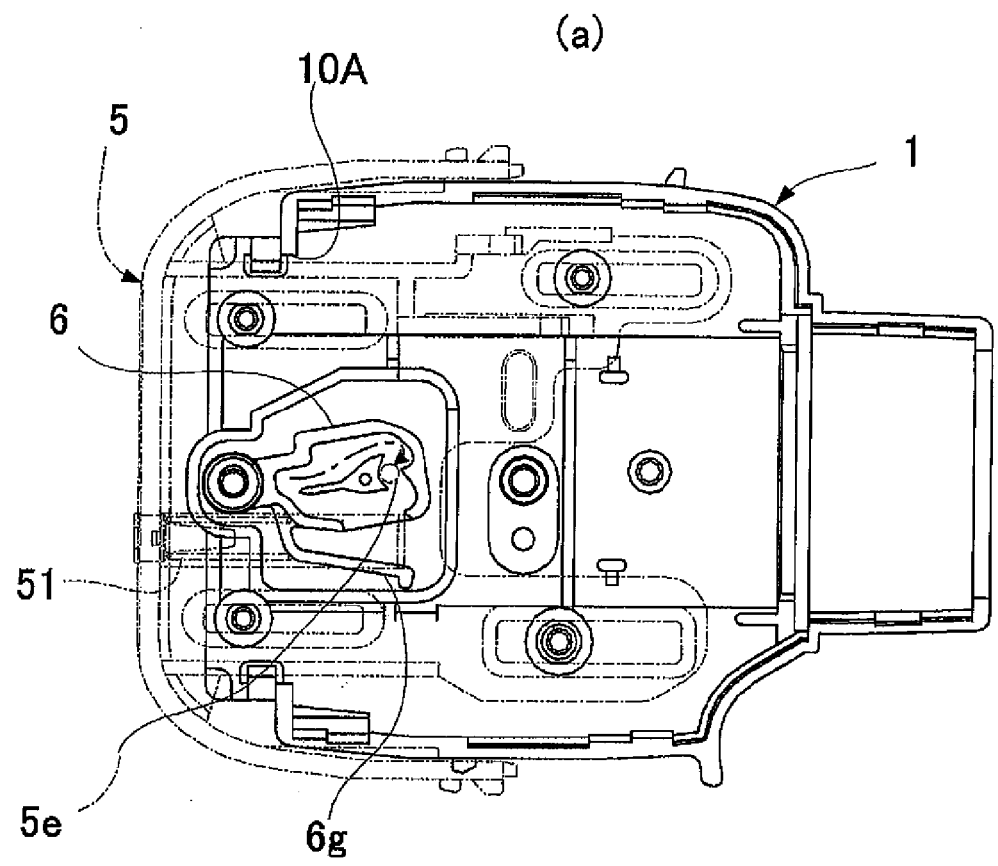
FIG. 16 is a plan view showing an operation for locking a bottom cap of the powder inhaler.
Figure 16:
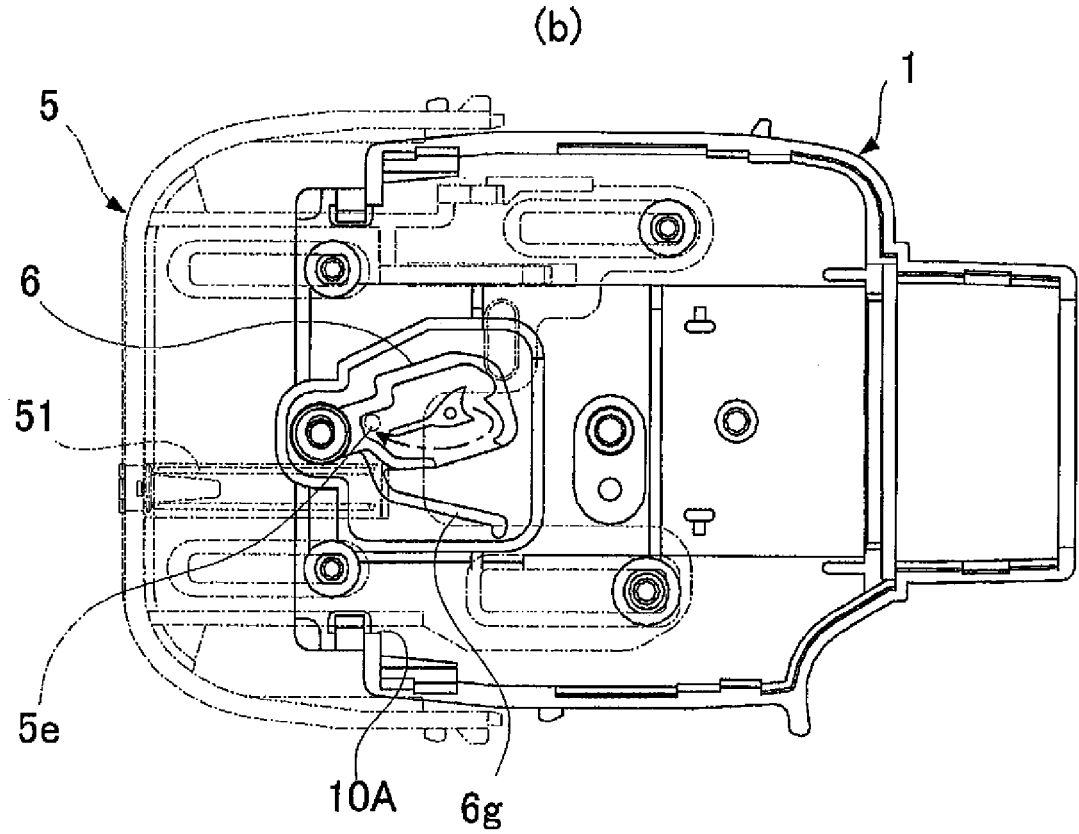

The connector 5 is formed to be movable back and forth in parallel to the housing body 1, and, as shown in FIG. 16, biased by a return spring (coil spring) 51 so that it protrudes externally through the opening 10A of the housing body 1. As shown in FIG. 3, the connector 5 includes a guide plate 5a that is provided with a latching long hole 5b for vibrating the drug carrier 4, and a guiding long hole 5c where a guide axis 1m for guiding the connector 5 is inserted. An engagement pin 5e is projected from the lower face of the guide plate 5a. The connector 5 has a projecting attachment axis 5f where the return spring 51 is mounted. A plate-type attachment section 5g for attaching the connector 5 to the bottom cap C1 extends from the back end of the guide plate 5a. A latching elastic jut 5i is formed on each end of the attachment section 5g. The latching elastic juts 5i are slightly deformed to be latched with latching projections 52A (FIG. 12) formed on both sides of the inner wall of the back of the bottom cap C1, thereby connecting the connector 5 and the bottom cap C1.

Figure 13:
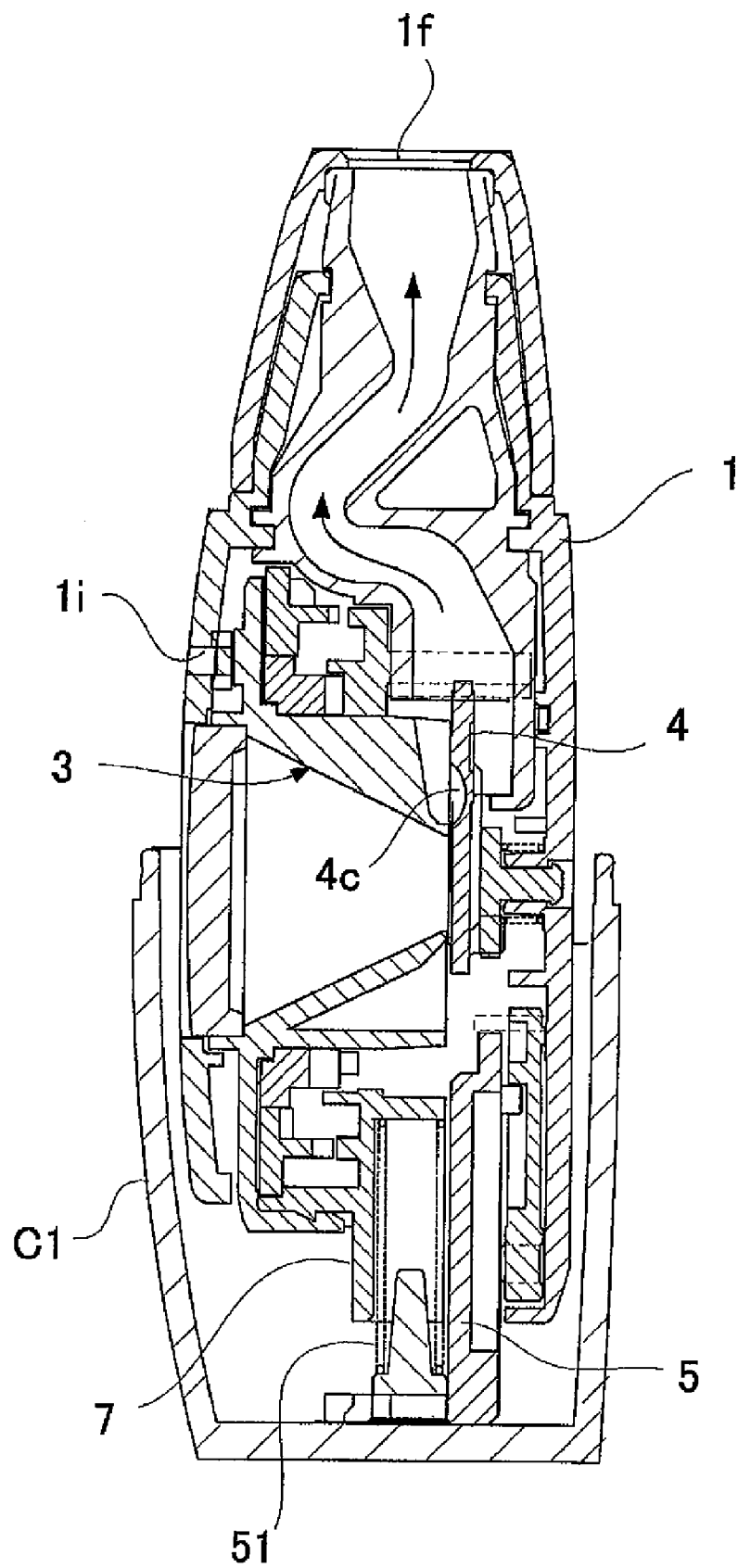
FIG. 13 is a vertical cross-sectional view showing powder inhalation using the powder inhaler.

As shown in FIGS. 2 and 13, the bottom cap C1 is fitted in the back of the housing body 1 to cover the opening 10A. The bottom cap C1 is also connected to the drug carrier 4 via the connector 5, which allows the bottom cap C1, while attached to the back of the housing body 1, to be movable backward and frontward with respect to the housing body 1.

As shown in FIG. 10, the locking member 6 includes a guide groove 6a, a pivot hole 6f and an elastic lever 6g. The guide groove 6a includes a first switching member 6b, a second switching member 6c, a front engagement member 6d and a back engagement member 6e. The locking member 6 is stored in the storage 1t of the lower housing body 1b, and the pivot axis 1p is fitted in the pivot hole 6f in the storage 1t. The connector 5 is disposed on the locking member 6, and the engagement pin 5e (see FIG. 3) of the connector 5 is inserted into the guide groove 6a in the locking member 6.

Figure 15:
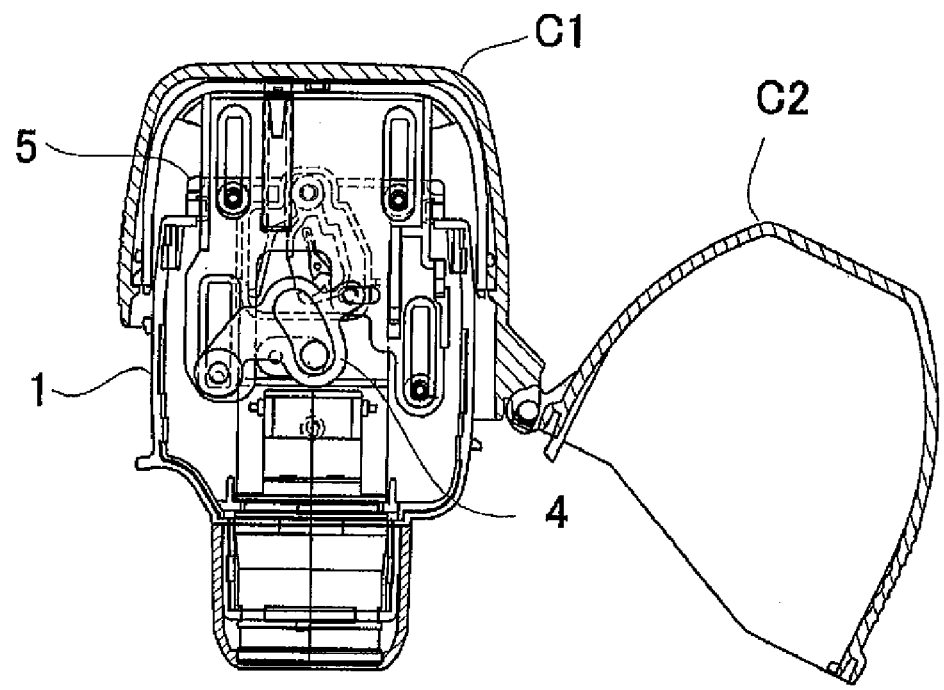
FIG. 15(a) is a plan cross-sectional view showing the powder inhaler before operation.
FIG. 15(b) is a plan cross-sectional view showing the powder inhaler after operation.
Figure 15:
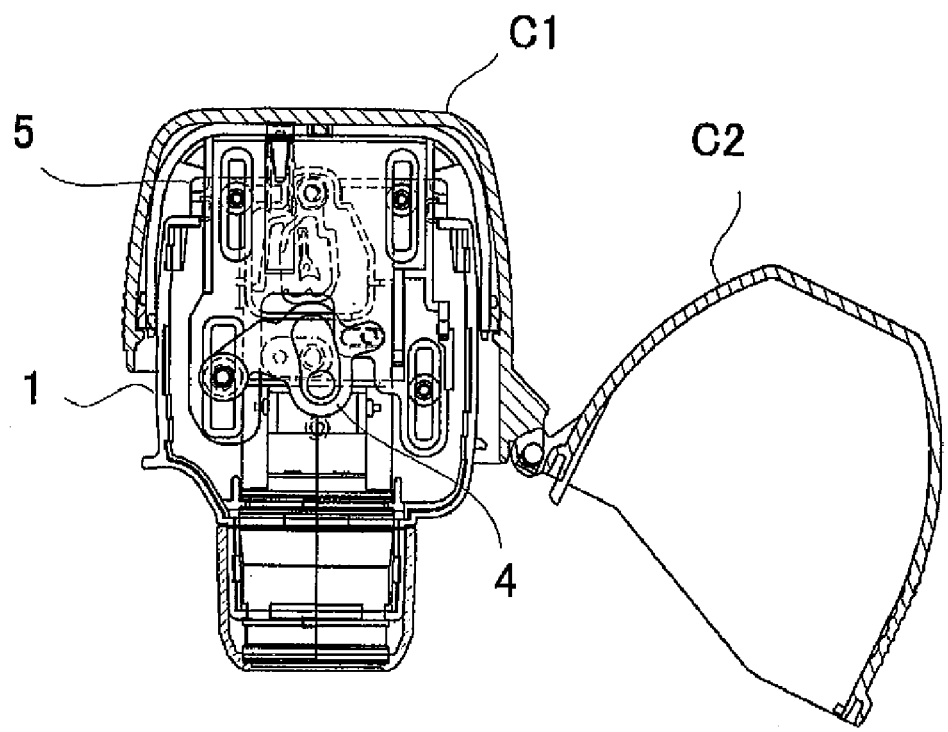

The following explains the mechanism of the locking member 6. As shown in FIGS. 10 and 16 at the drug-receiving position (original position; denoted by (b) in FIG. 16), where the drug discharge outlet 3b meets the measurement concave portion 4c, the engagement pin 5e of the connector resides in the back engagement member 6e, and the connector 5 and the bottom cap C1 protrude from the back side of the housing body 1 to the maximum extent by the elastic force of the return spring 51. By pushing the housing body 1 in this position into the bottom cap C1, the engagement pin 5e of the connector 5 connected to the bottom cap C1 passes through the back engagement member 6e of the locking member 6 and the guide groove 6a to reach the first switching member 6b (see FIG. 16 (a)). As a result, the locking member 6 oscillates by its own resistivity against the elastic force of the elastic lever 6g. Thereafter, when the pushing force exerted to the housing body 1 is released, the engagement pin 5e of the connector 5 is engaged with the front engagement member 6d due to the elastic force of the return spring 51, thereby locking the housing body 1 fitted in the bottom cap C1. As shown in FIG. 15, the measurement concave portion 4c moves from the drug discharge outlet 3b to the admission port 2f (to the front), residing in the drug-inhalation position at which the user can inhale the drug from the admission port 2f. In this state, the drug carrier 4 is prevented from moving from the drug-inhalation position to the drug-receiving position. Then, the housing body 1 is pushed again into the bottom cap C1 to a predetermined extent, the elastic recovery force of the elastic lever 6g of the locking member 6 releases the engagement pin 5e from the front engagement member 6d. The released engagement pin 5e reaches the second switching member 6c (FIG. 16 (b)), thereby unlocking the lock mechanism. Then, by releasing the force of pushing the housing body 1 into the bottom cap C1, the elastic force of the return spring 51 moves the engagement pin 5e to the back engagement member 6e through the guide groove 6a, and the bottom cap C1 and connector 5 return to the original position (drug receiving position) (FIG. 16 (b)). The operation of the entire powder inhaler is described later.

Figure 18:
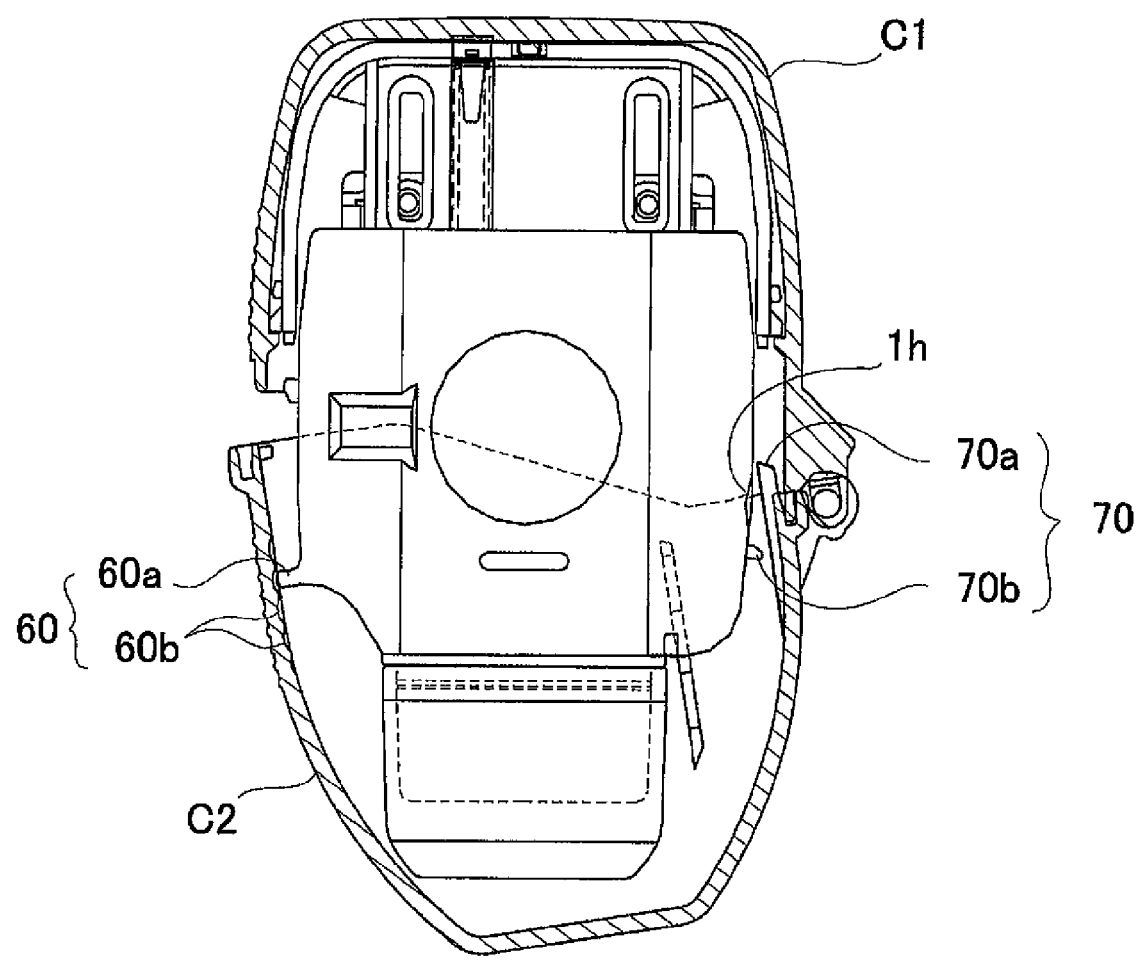
FIG. 18 is an explanatory view for showing operation of the powder inhaler.
Figure 19:
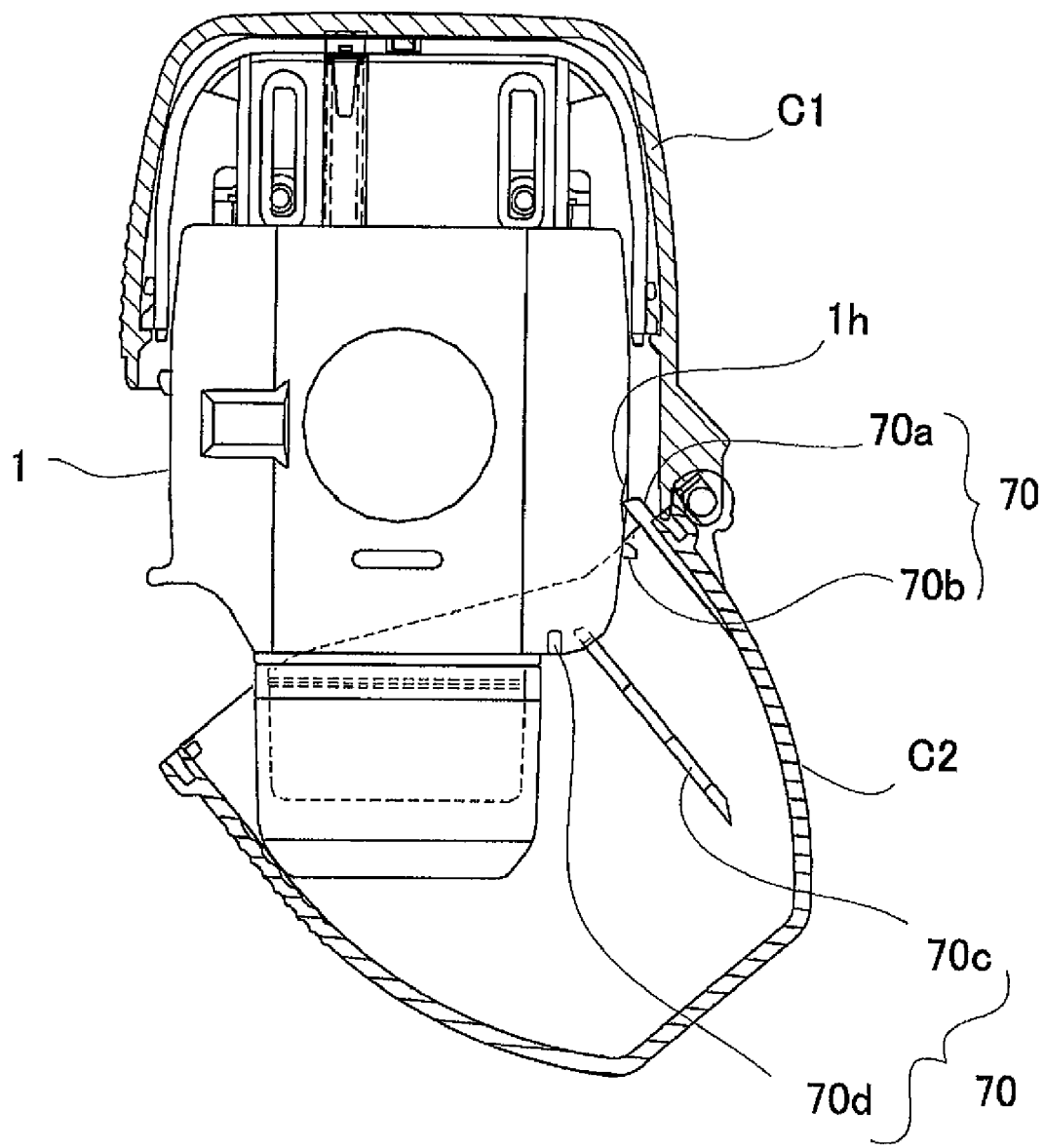
FIG. 19 is an explanatory view for showing operation of the powder inhaler.

As shown in FIGS. 18 and 19, a lock-releasing engagement member 70 is made of two parts formed on the internal lateral face of the cover cap C2 and the external lateral face of the housing body 1, respectively. The two parts of the lock-releasing engagement members 70 are engaged with each other when the cover cap C2 is closed so as to push the housing body 1 into the bottom cap C1 to a predetermined extent.

Figure 20:
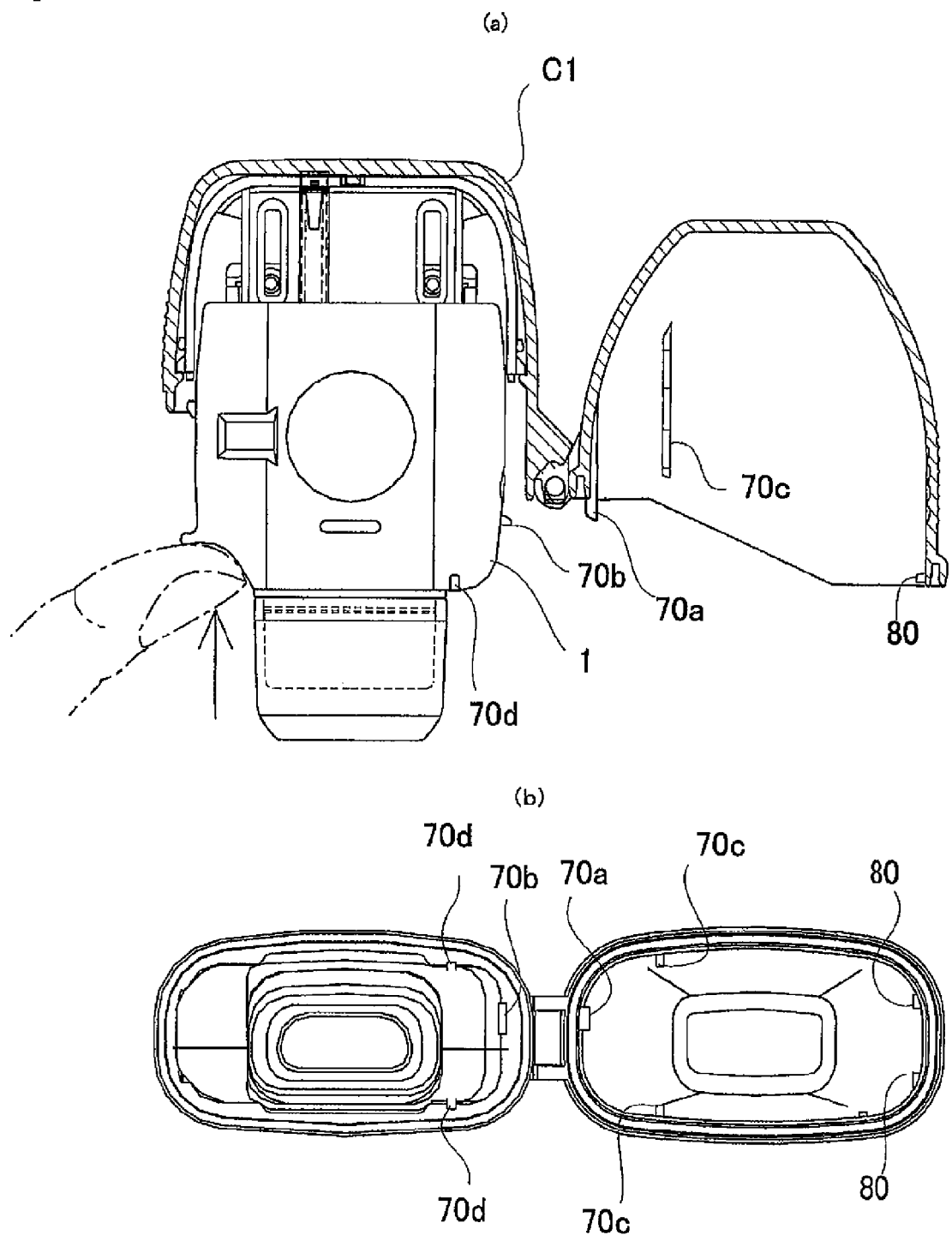
FIGS. 20(a) and 20(b) are a front view and a plan view, respectively, for showing operation of the powder inhaler.
Figure 22:
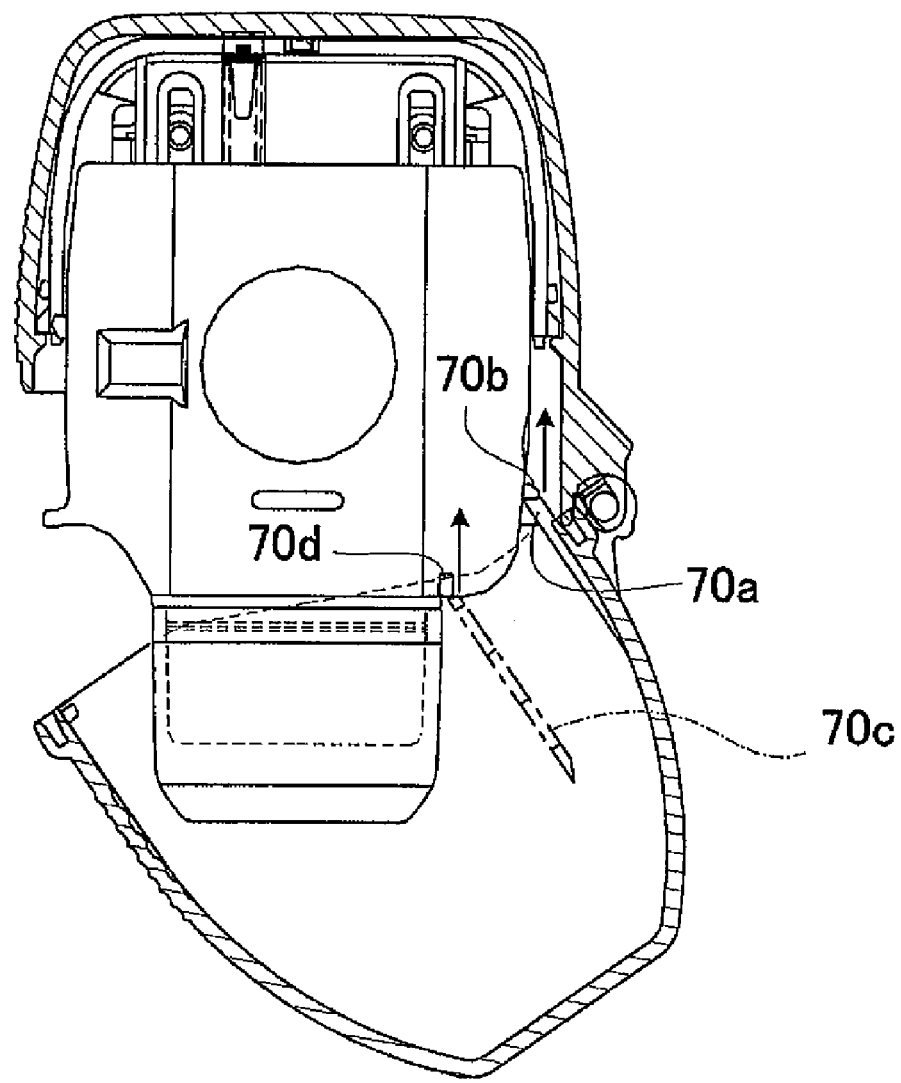
FIG. 22 is an explanatory view for showing operation of the powder inhaler.

The lock-releasing engagement member 70 is more specifically made of latching projections 70a and 70c (FIGS. 22, 20(b)) formed inside the cover cap C2, a latch-receiving projection 70b formed on the lateral face of the housing body 1 to be latched with a latching projection 70a, and latch-receiving projections 70d (FIGS. 22, 20(b)) formed on the front end of the upper and lower faces of the housing body 1 to be latched with a latching projection 70c.

The latching projections 70a and 70c are designed to each have predetermined lengths to ensure the following operation. Specifically, while the cover cap C2 is closing the housing, the latching projections 70a and 70c are engaged with the latch-receiving projections 70b and 70d for the distance only enough to release the lock when moving the engagement pin 5e of the connector 5 from the front engagement member 6d to the second switching member 6c. By the design, the latching projections 70a and 70c are then disengaged from the latch-receiving projections 70b and 70d when the cover cap C2 is completely closed (see FIG. 22). Accordingly, when the cover cap C2 is completely closed, the lock mechanism provided by the locking member 6 is released, and the elastic force of the return spring 51 causes the housing body 1 to stick out and return to the drug receiving position (original position). The lock-releasing engagement member 70 is not limited to the one shown in the figure, but may have a variety of forms.

Figure 5:
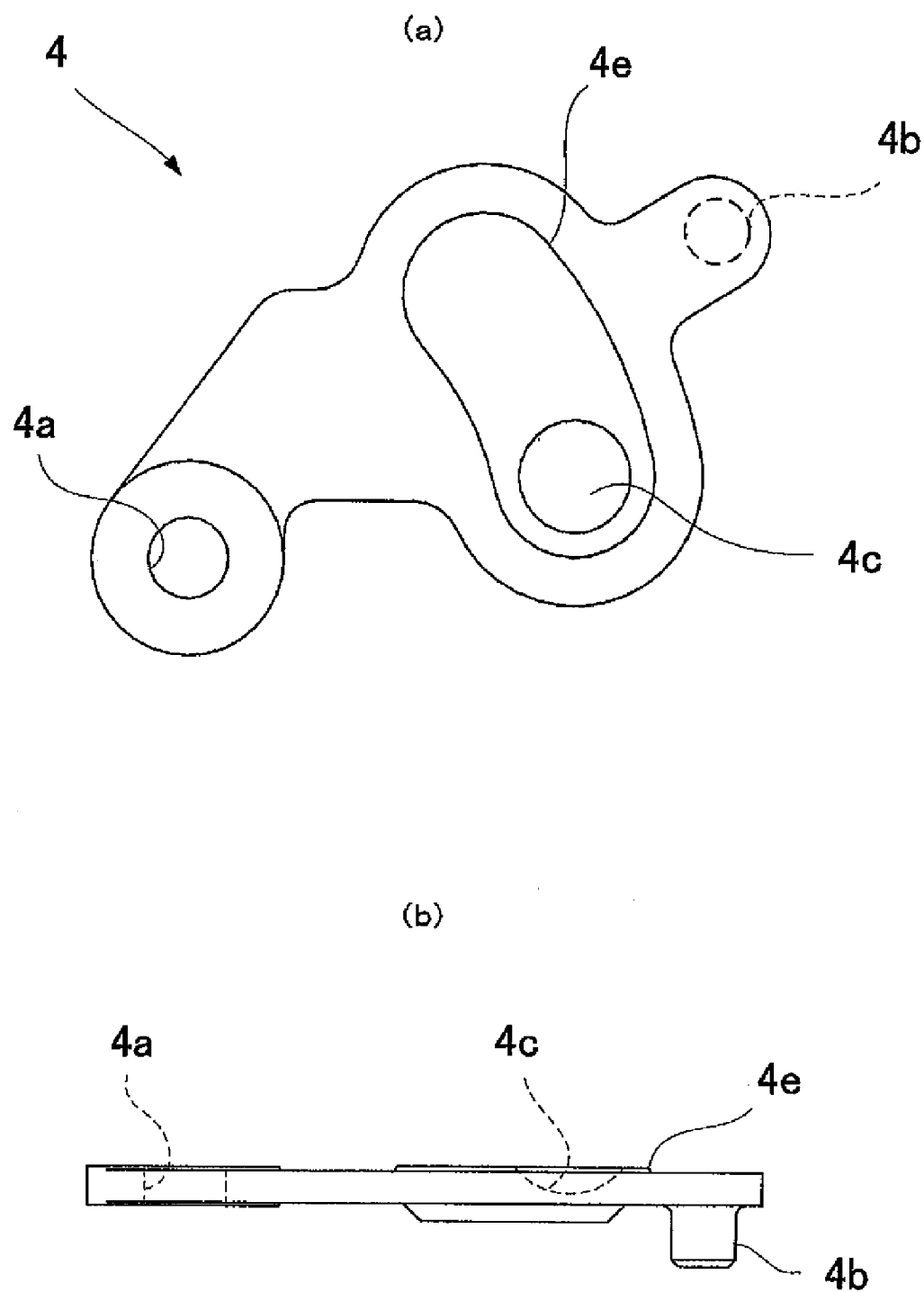
FIGS. 5(a) and 5(b) are a plan view and a lateral view, respectively, of a drug carrier of the powder inhaler.

As shown in FIG. 5, one end of the drug carrier 4 has an axis hole 4a, and the other end has a latching pin 4b. A measurement concave portion 4c having a spherically concave shape is formed in the intermediate portion between the axis hole 4a and the latching pin 4b. The measurement concave portion 4c has an area corresponding to the volume of a single dose of a drug.

A part of the upper face of the drug carrier 4 has a slight rise, which serves as a sliding portion 4e. The sliding portion 4e has a circular arc shape in a plan view. On one end of the sliding portion 4e, a measurement concave portion 4c is formed. With this structure, when the measurement concave portion 4c moves forward and backward on the circular arc track, only the sliding portion 4e of the drug carrier 4 comes in contact with the lower face of the thick portion 3g around the drug discharge outlet 3b of the supplier 3.

As described later, the drug carrier 4 is pivotally supported on the guide axis 1m projected from the inner wall of the lower housing body 1b. The latching pin 4b of the drug carrier 4 is inserted to the latching long hole 5b of the connector 5 to engage the drug carrier 4 with the connector 5.

Figure 6:
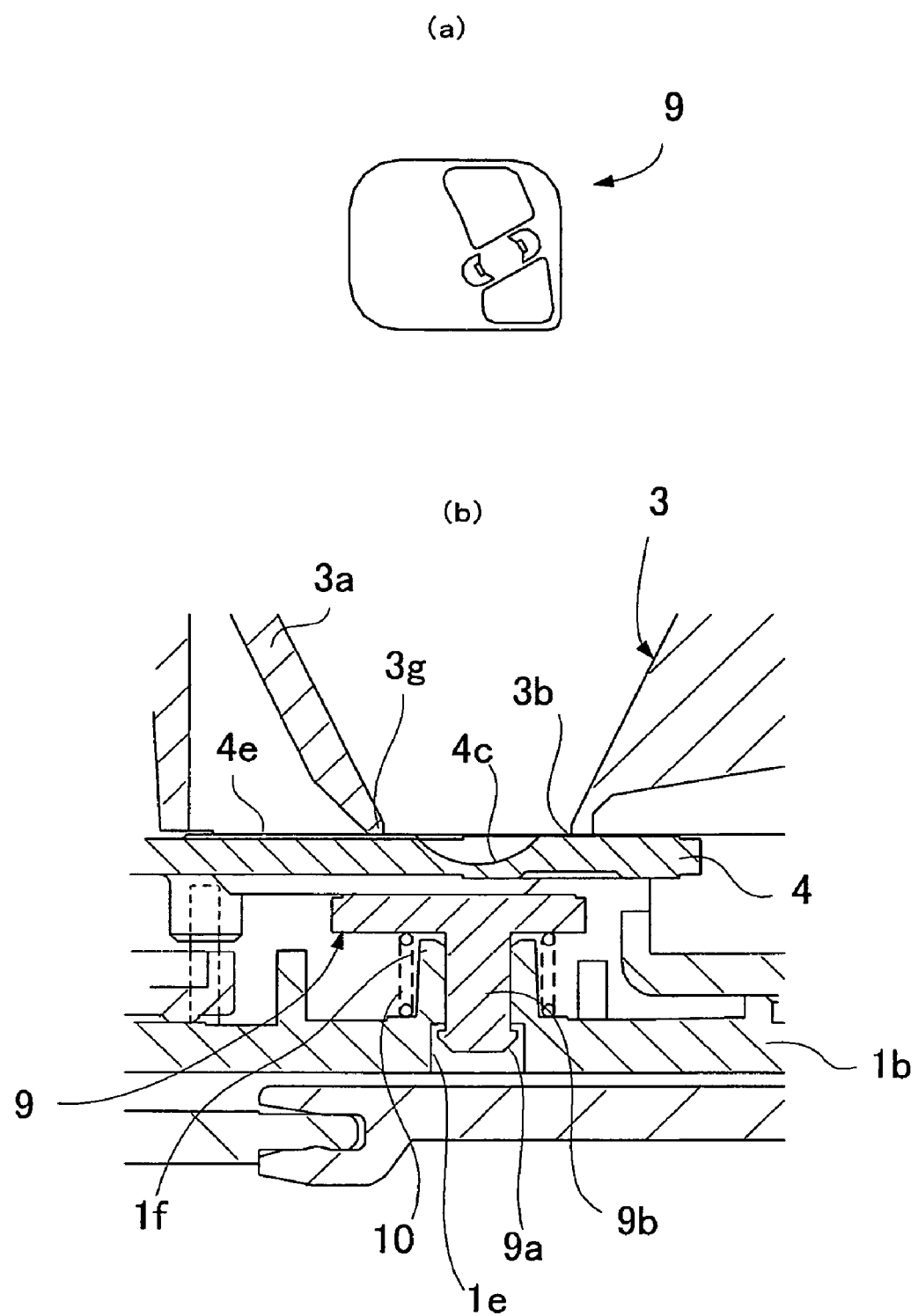
FIG. 6(a) is a plan view of a pusher of the powder inhaler.
FIG. 6(b) is a cross-sectional view showing a state where the pusher is attached to the base.

Further, as shown in FIG. 6, the drug carrier 4 is biased upward by the pusher 9 (described later), so that the sliding portion 4e of the drug carrier 4 comes in contact with the lower face of the thick portion 3g around the drug discharge outlet 3b of the supplier 3. With this structure, the sliding portion 4e of the drug carrier 4 becomes more tightly close to the periphery of the discharge outlet 3b of the supplier 3, thereby preventing leakage of the fine powder drug from the measurement concave portion 4c of the drug carrier 4.

Figure 4:
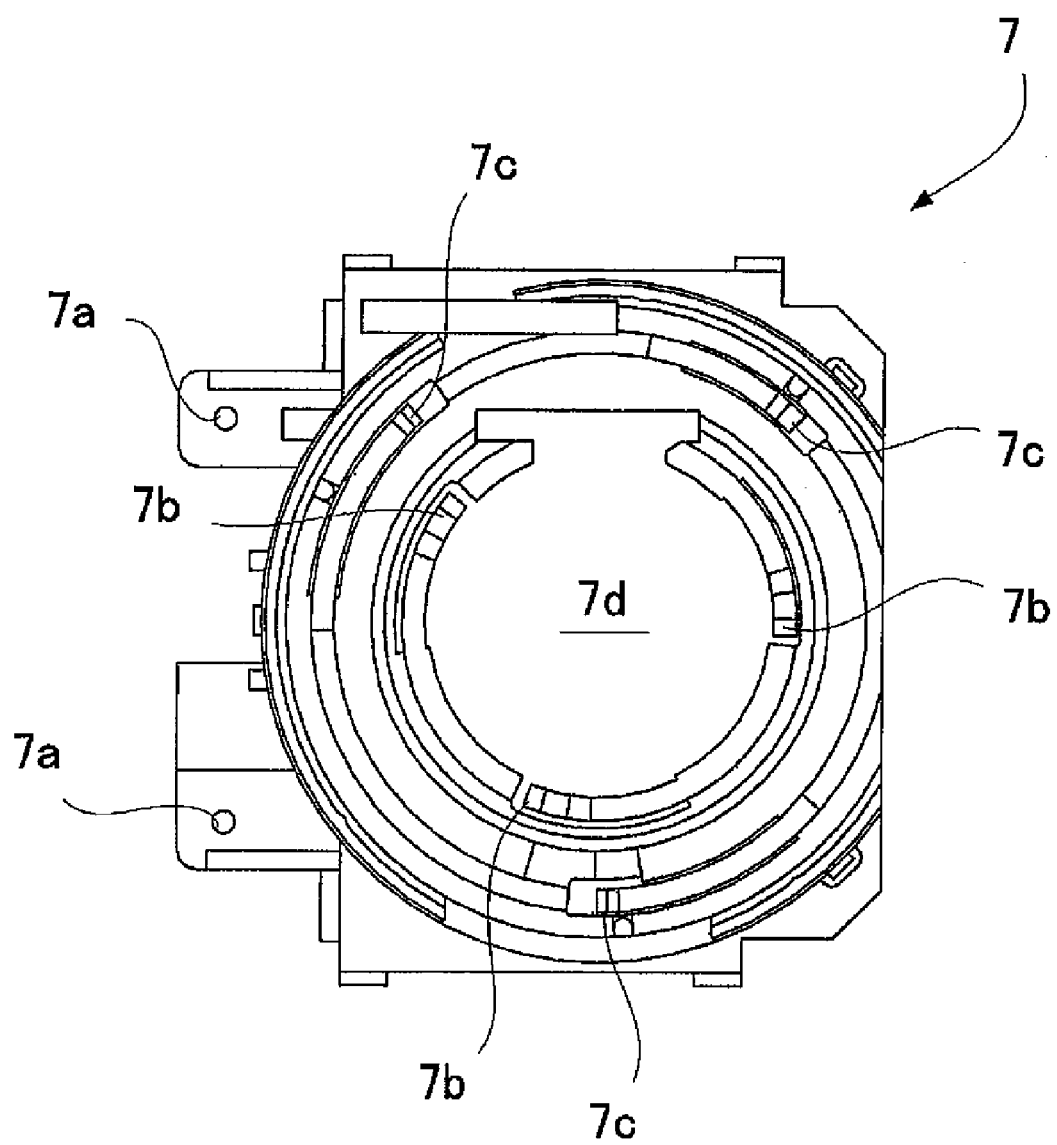
FIG. 4 is a plan view of a base of the powder inhaler.

As shown in FIG. 4 etc., the base 7 includes an inset hole 7a, a circular opening 7d for storing the hopper 3a, and counter-supporting pawls 7b and 7c circularly provided around the circular opening 7d.

Further, as shown in FIG. 6, the lower housing body 1b includes an attachment hole 1e and a spring-supporting axis 1f. A pushing spring 10 for pushing up the pusher 9 is disposed around the exterior of the spring-supporting axis 1f. The lower face of the pusher 9 is provided with a holding axis 9b that has a retaining member 9a on its top end. The holding axis 9b is inserted in the attachment hole 1e. As shown in FIG. 6 (b), the pusher 9 is biased upward by the pushing spring (coil spring) 10.

Figure 17:
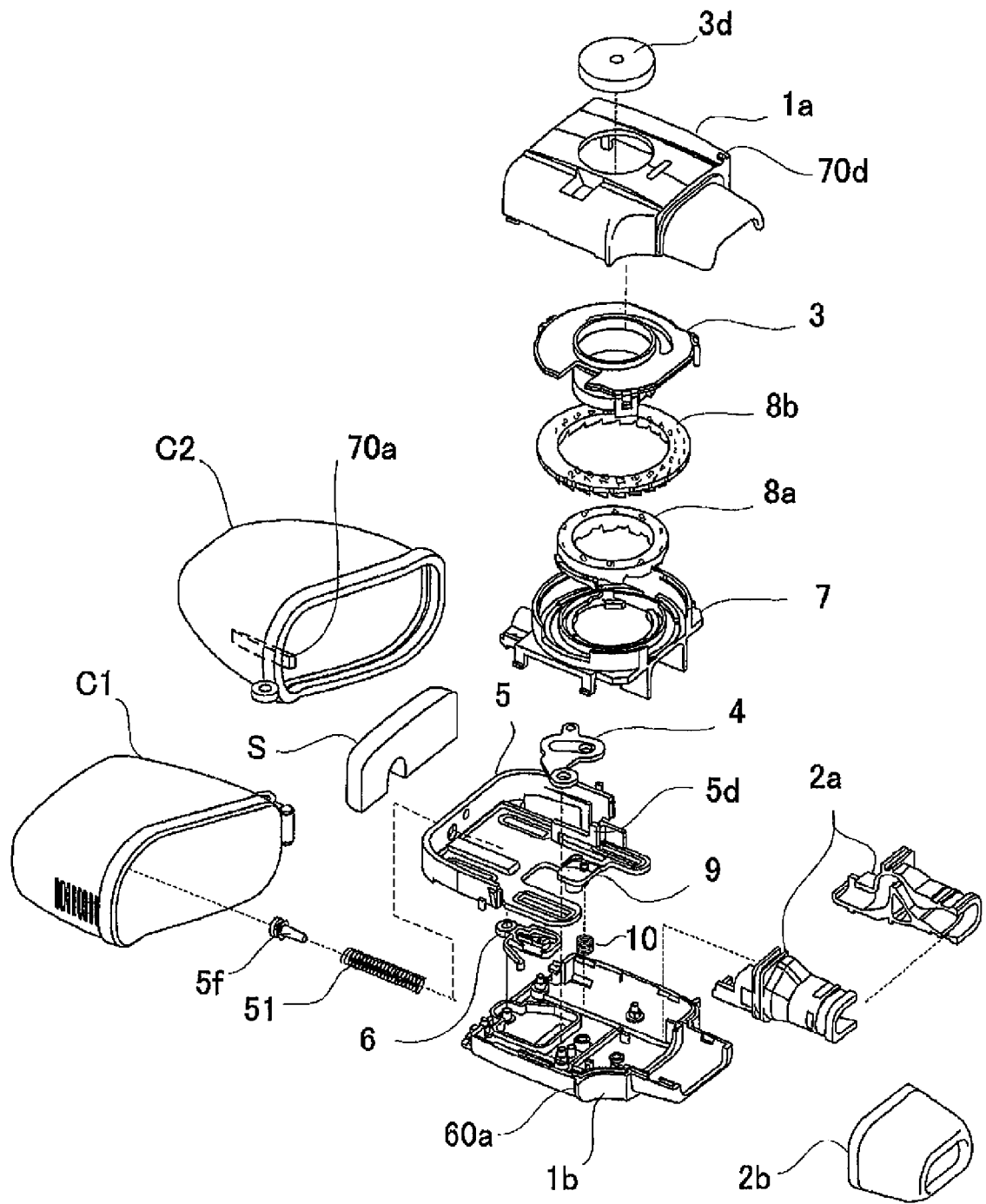
FIG. 17 is an exploded perspective view of the powder inhaler.

The connector 5 is provided with a ratchet-driving pawl 5d that is engaged with the counter 8 and rotates the counter 8 in response to the forward and backward movement (FIG. 3, FIG. 17).

Figure 7:
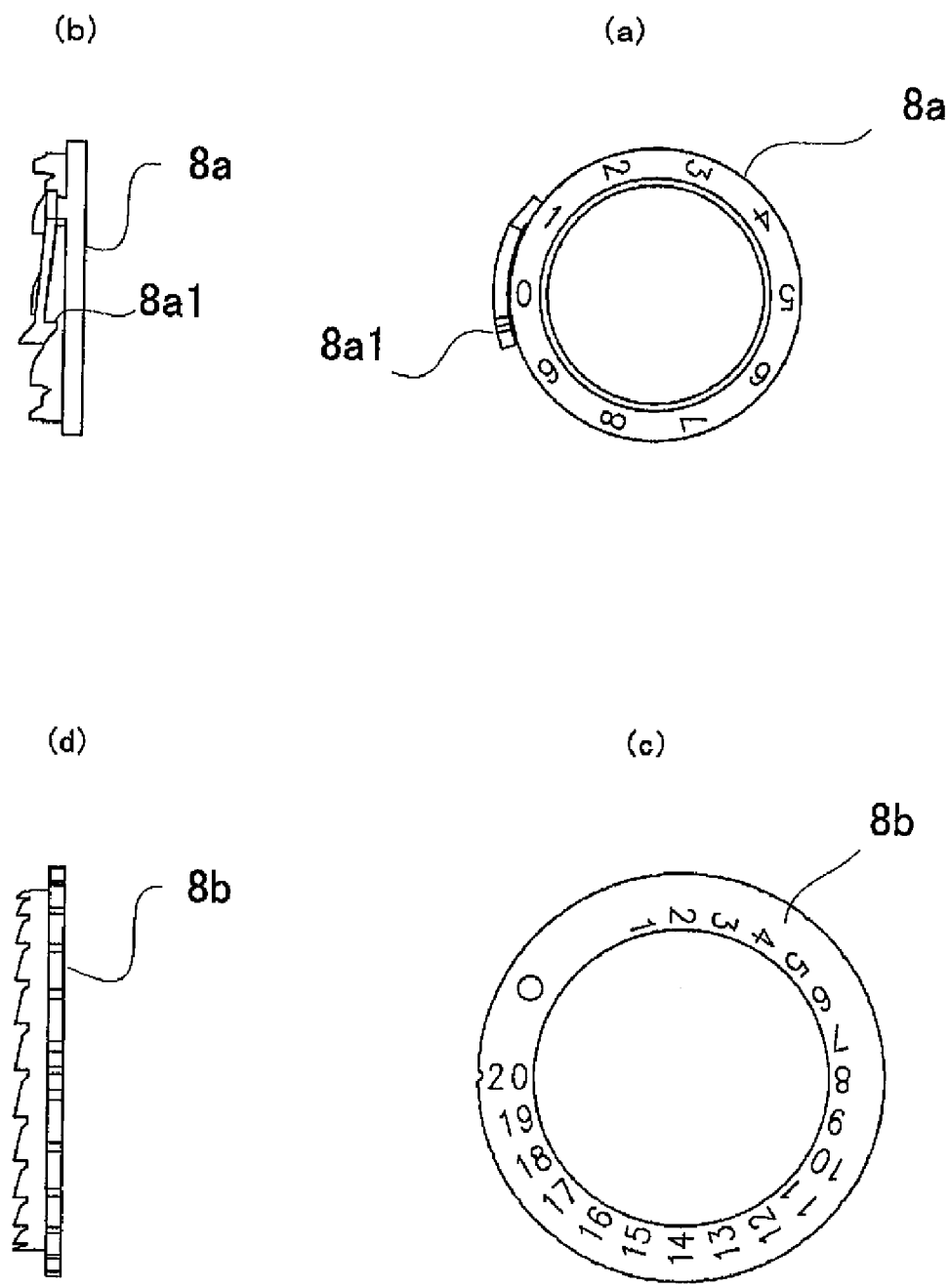
FIG. 7 is a plan view showing a counter of the powder inhaler.

As shown in FIG. 7, the counter 8 has a structure according to a known art, provided with an inner circular ring 8a denoting a unit's place and an outer wheel 8b denoting a ten's place. The circular ring 8a includes a tube ratchet (see FIG. 7 (b)), and is supported by a counter-supporting pawl 7b formed on the base 7 so that it rotates in one direction. The wheel 8b also has a tube ratchet (see FIG. 7 (d)), and is supported by a counter-supporting pawl 7c formed on the base 7 so that it rotates in one direction.

With this structure, when the drug carrier 4 pivots, the ratchet-driving pawl 5d causes only the circular ring 8a denoting a unit's place to rotate. A ratchet-driving pawl 8a1 is formed on the outer circumference of the circular ring 8a and drives the wheel 8b by rotating it along the outer circumference. At the tenth dose, the wheel 8b rotates for the length corresponding to the scale "1". The wheel 8b has scales from 1 to 20, and is combined with the circular ring 8a to display 1 to 200 doses.

Alternatively, an electric conduction filler such as carbon may be given to the materials of supplier 3, the drug carrier 4, and the connector 5 to provide them with electric conduction so as to induce electrostatic leakage.

Note that, such electric conduction may also be given to components other than the supplier 3, the drug carrier 4 and the connector 5.

The powder inhaler is assembled as follows.

Figure 11:
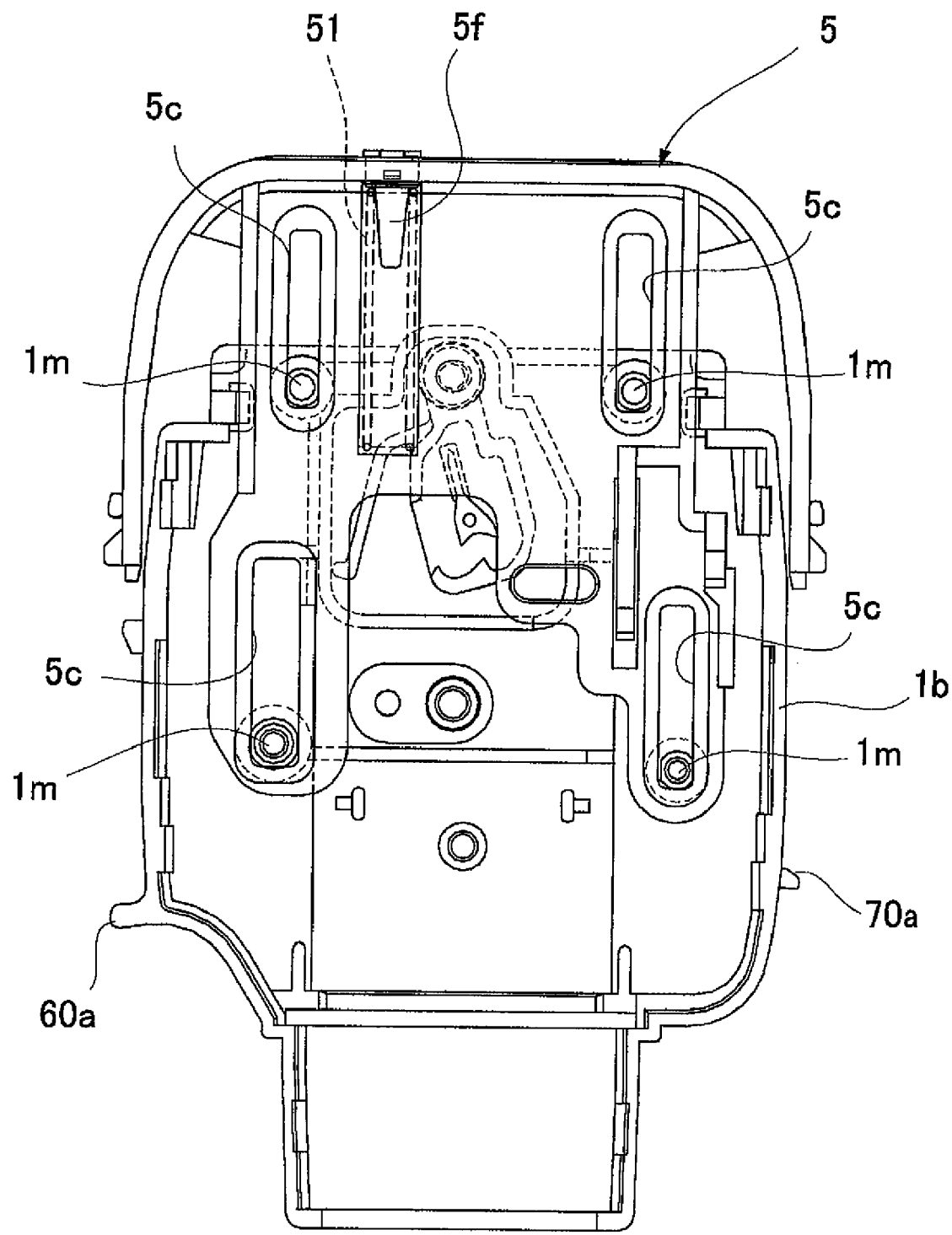
FIG. 11 is a plan view showing an order of assembly of the powder inhaler.

An interdigitation groove 2e of the mouthpiece 2 is fitted in the pinch projection 1g of the lower housing body 1b. Further, the locking member 6 is stored in the storage 1t of the lower housing body 1b as shown in FIG. 10. Then, as shown in FIG. 11, the connector 5 is attached to the lower housing body 1b to be disposed on the locking member 6. Simultaneously, the guide axis 1m of the lower housing body 1b is inserted in the guiding long hole 5c of the connector. Further, the return spring 51 is inserted in the attachment axis 5f of the connector 5 so that the front end of the return spring 51 is engaged with the spring engaging projection 7q formed on the base 7 (see FIG. 2).

Next, after the pusher 9 is mounted to the base 7 in the foregoing manner, the drug carrier 4 is installed on the pusher 9. At this time, one of the guide axes 1m of the lower housing body 1b is inserted in the axis hole 4a of the drug carrier 4 (FIG. 12), and the latching pin 4b of the drug carrier 4 is inserted in the latching long hole 5b of the connector so that the drug carrier 4 is engaged with the connector 5. The drug carrier 4 is pivotably supported by the axis hole 4a.

Figure 12:
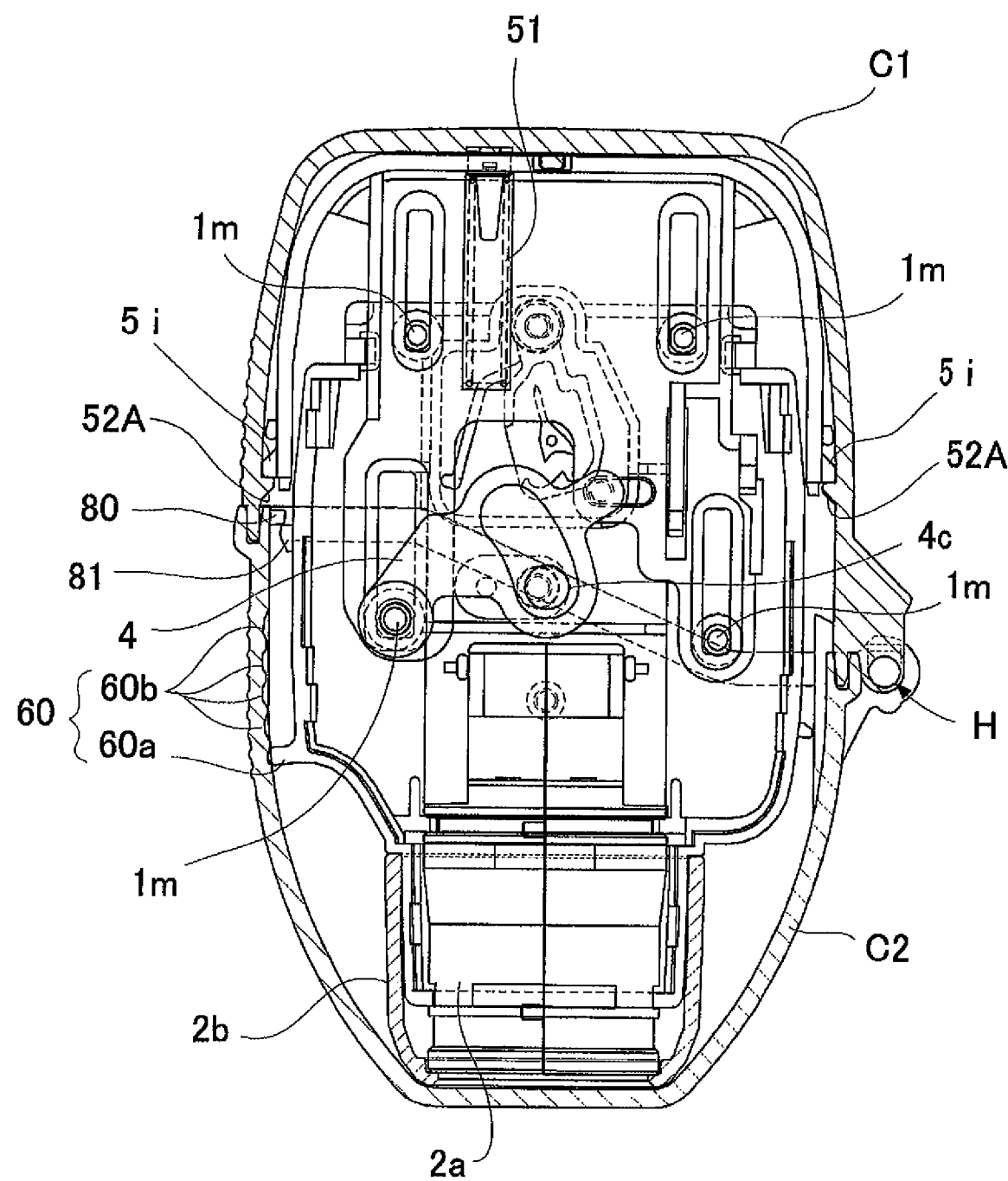
FIG. 12 is a plan view showing an order of assembly of the powder inhaler.

Next, as shown in FIG. 12, the base 7 is placed in the lower housing body 1b through the drug carrier 4 and the connector 5. At this time, the inset hole 7a of the base 7 is fitted in two of the guide axes 1m of the lower housing body 1b to adjust the position of the base 7. Thereafter, the circular ring 8a and the wheel 8b for constituting the counter 8 are stored in the base 7.

Then, as shown in FIG. 2, the supplier 3 is inserted in the circular ring 8a so that the supplier 3 is disposed on the drug carrier 4. A cover 3d is attached to the supplier 3.

Next, the upper housing body 1a is joined to the lower housing body 1b. The pinch projection 1g (FIG. 2) of the upper housing body 1a is fitted in the interdigitation groove 2e of the mouthpiece 2, and the cover 2b is fitted in the main body 2a of the mouthpiece 2.

Further, as shown in FIG. 12, the bottom cap C1 is fitted in the back portion of the housing body 1, and the latching projection 52A is engaged with the latching elastic jut 5i of the connector 5. FIG. 12 omits some components, including the supplier 3.

The following describes the operation of the powder inhaler with such an arrangement.

First, as shown in FIG. 2, with the cover cap C2 on, the drug carrier 4 is in the drug-receiving position where the measurement concave portion 4c of the drug carrier 4 meets the drug discharge outlet 3b of the supplier 3.

As shown in FIGS. 12 to 15, FIG. 18, and FIG. 23, the housing body 1 is vibrated by the vibrating means 60 as the cover cap C2 is opened. More specifically, with the operation of opening the cover cap C2, the housing 1 is pushed by the convex portion 60a, which has been disengaged from the concave portion 60b and passes through the rise between the adjacent concave portions 60b before being engaged with the next concave portion 60b. This movement of the convex portion 60a vibrates the housing body 1. Further, as shown in FIG. 23, as the cover cap C2 is opened, the housing body 1 is pushed by the projection of the convex portion 60d when the convex portion 60d passes through the convex portions 60c, and the housing body returns to the original position after the convex portion 60d passed through the convex portions 60c. This also vibrates the housing body 1. Further, collision between the convex portion 60a and the concave portion 60b, or collision between the convex portion 60d and the convex portion 60c also causes vibration of the housing body 1. As a result, the convex portions 60a and 60c sequentially slide on and are engaged with the concave portions 60b and the convex portions 60d, respectively. This "sliding engagement" causes the vibration of the housing body 1. The vibration of the housing body 1 further causes the vibration of the supplier 3 fixed to the housing body 1. The vibration of the supplier 3 makes the fine particle drug contained in the supplier 3 travel along the slope of the hopper 3a, thereby sending the particle drug to the drug-discharging outlet 3b. As a result, the measurement concave portion 4c in the drug carrier 4 is filled with the fine particle drug. A concave part 1h is formed on the outer wall of the housing body 1 to avoid interference of the latching projection 70a with the housing body 1 when the cover cap C2 is opened (see FIG. 19).

Figure 21:
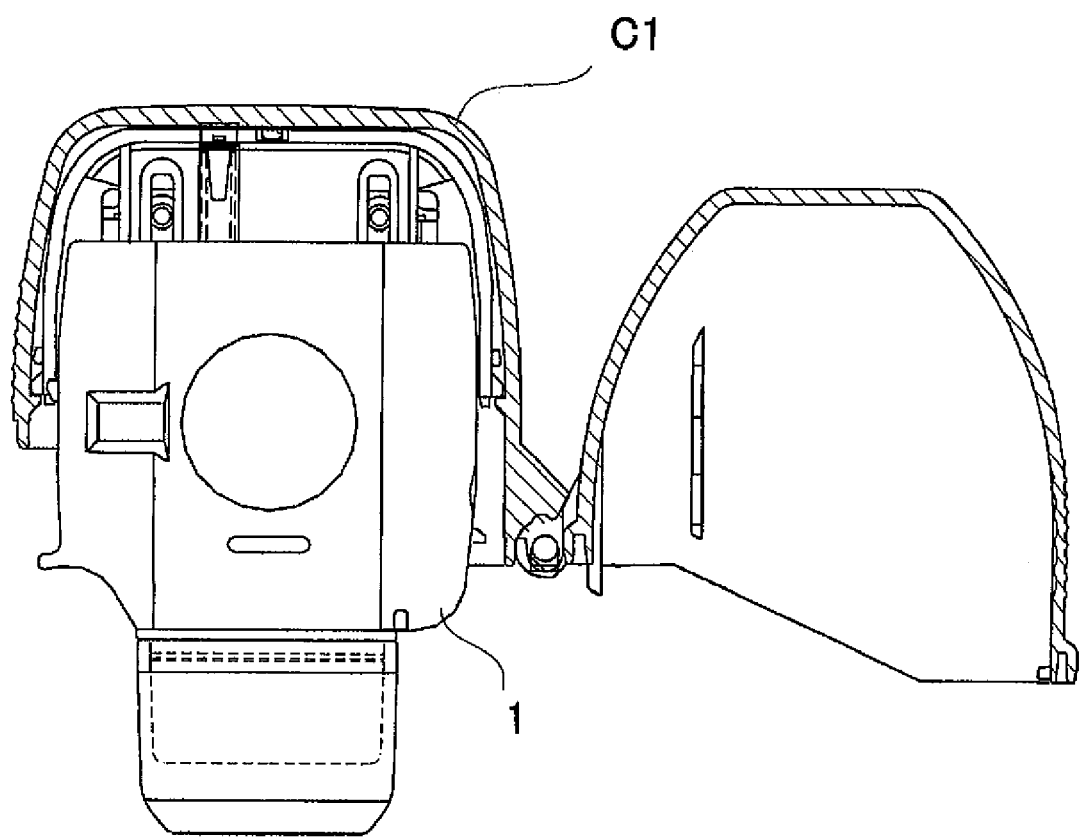
FIG. 21 is an explanatory view for showing operation of the powder inhaler.

When the housing body 1 is pushed into the bottom cap C1 while holding the bottom cap C1, (FIG. 20), the first switching member 6b blocks the insertion of the housing body 1 at a certain point, and the connector 5 is locked by the locking member 6 at the drug inhalation position because of the engagement with the engagement member 6d. As the housing body 1 is pushed down, the drug carrier 4 is pivoted, and the measurement concave portion 4c moves from the drug-receiving position to the drug-inhalation position provided in the space of the hopper 3a communicating with the drug-inhalation path 2c (FIG. 21).

In response to the pivot of the drug carrier 4, the fine powder drug contained in the measurement concave portion 4c is scraped by the thick portion 3g around the drug discharge outlet 3b. The single dose of the drug thus scraped is then transferred to the drug-inhalation position in the space connected to the drug-inhalation path 2c.

Next, when the patient inhales air from the housing 1A through the admission port 2f of the mouthpiece 2 using his/her own intake pressure, the pressure inside the housing 1A becomes negative, and external air is absorbed into the housing body 1 through the air inlet 1i. As shown by the arrow in FIG. 13, the absorbed air enters into the drug-inhalation path 2c of the mouthpiece 2, and gives an impact to the fine powder drug contained in the measurement concave portion 4c of the drug carrier 4, thereby causing the fine powder drug to disperse in the drug-inhalation path 2c of the mouthpiece 2. The dispersed powder is carried by the inhaled air through the admission port 2f, entering the lungs of the patient.

After inhalation is completed, the cover cap C2 is closed. When the cover cap C2 is closed, the respective parts of the lock-releasing engagement member 70 are engaged (FIG. 22). On the engagement of the lock-releasing engagement member 70, the housing body 1 resides in the drug-inhalation position by being pushed into the bottom cap C1. Therefore, the first engagement section and the second engagement section of the vibrating means 60 are away from each other and do not engage. The lock-releasing engagement member 70 pushes the housing body 1 into the bottom cap C1 only to the extent with which the locking member 6 releases the lock. Accordingly, the released housing body 1 returns to the drug-receiving position due to the elastic force of the return spring 51. With this operation to return the housing body 1 to the original position (the drug-receiving position), the drug carrier 4 swings back, and the measurement concave portion 4c returns to the drug-filling position beneath the drug-discharge outlet 3b of the supplier 3.

When the user pushes the bottom cap C1 as shown in FIG. 14 (b) and FIG. 21, the window 1j to exhibit the counter 8 is covered by the bottom cap C1; therefore, the user will not see the moment when the dose number of the counter 8 displayed in the window 1j is switched. As such, the window 1j always displays the renewed counter 8, and the user will not be confused about the dose number.

As shown in FIG. 2, when the device is not used (e.g., when the device is carried), the cover cap C2 is closed to meet the back end of the cover cap C2 and the front end of the bottom cap C1 to make the housing 1A airtight. When the cover cap C2 is closed, for example, because the device is carried, the housing body 1 is biased to the cover cap C2 due to the elastic force of the return spring 51. To prevent the housing 1A from wobbling in the bottom cap C1 and cover cap C2 while the device is carried, as shown in FIG. 12, an engaging projection member 80 (see FIG. 20) is formed in the inner wall of the opening end of the cover cap C2, and an engagement-receiving projection member 81 is formed on the periphery of the housing body 1. The engaging projection member 80 is disengaged from the engagement-receiving projection member 81 in response to the opening movement of the cover cap C2.

The powder inhaler is discarded after the fine powder drug in the hopper 3a runs out.

To increase the moisture-proof properties of the powder inhaler, a tablet-type desiccant S may be attached inside the powder inhaler.

To ensure the desired properties, the bottom cap C1 and cover cap C2 are preferably made of a material having low water vapor permeability, such as high-density polyethylene or polypropylene.

The following describes the Second Embodiment of the powder inhaler according to the present invention, with reference to FIGS. 24 to 49. Throughout the figures, the same numerals are given to constituents identical to those of the First Embodiment, and their descriptions may be omitted.

Figure 24:
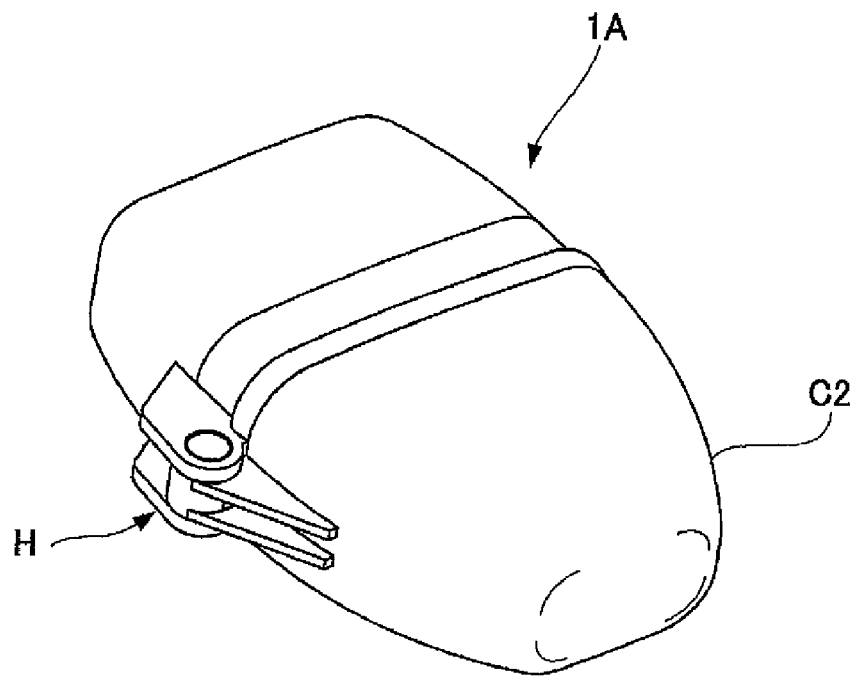
FIG. 24 is a perspective view of the appearance of the powder inhaler according to the Second Embodiment of the present invention.
Figure 25:
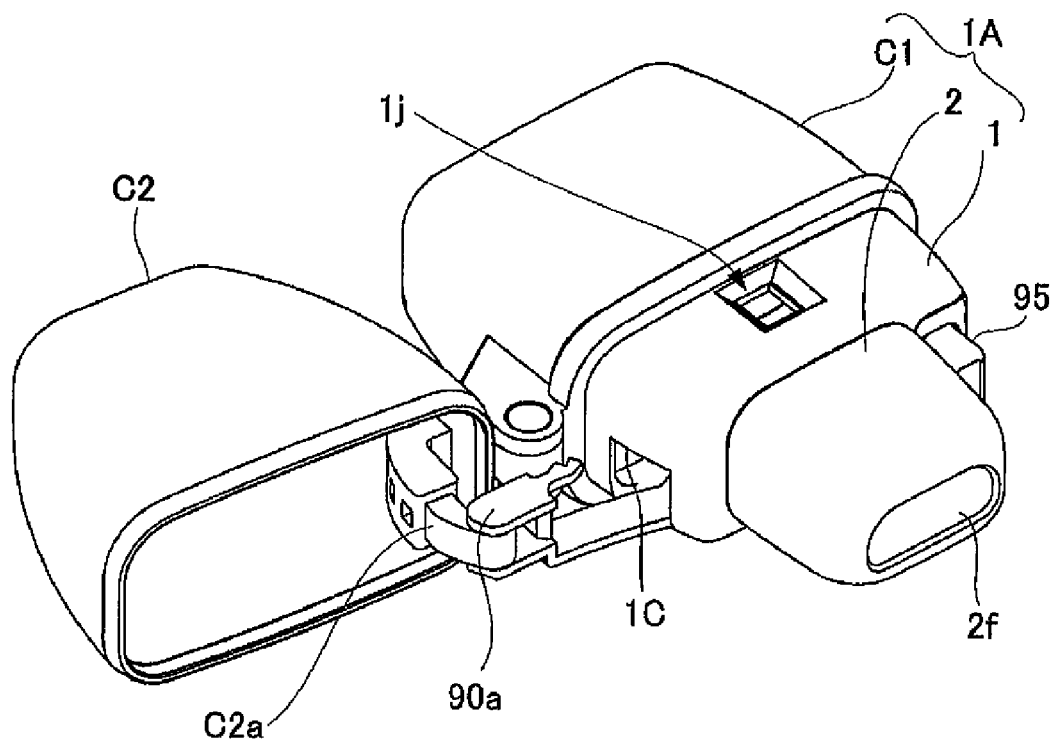
FIG. 25 is a perspective view of the powder inhaler according to the Second Embodiment, with a cover cap opened.

FIG. 24 is a perspective view of the appearance of the powder inhaler with the cover cap C2 closed. FIG. 25 is a perspective view of the appearance of the powder inhaler with a cover cap opened.

As shown in FIGS. 24 and 25, the powder inhaler includes a housing 1A with a suction end 2f, and a cover cap C2 pivotably connected to the housing 1A via a hinge H.

Figure 26:
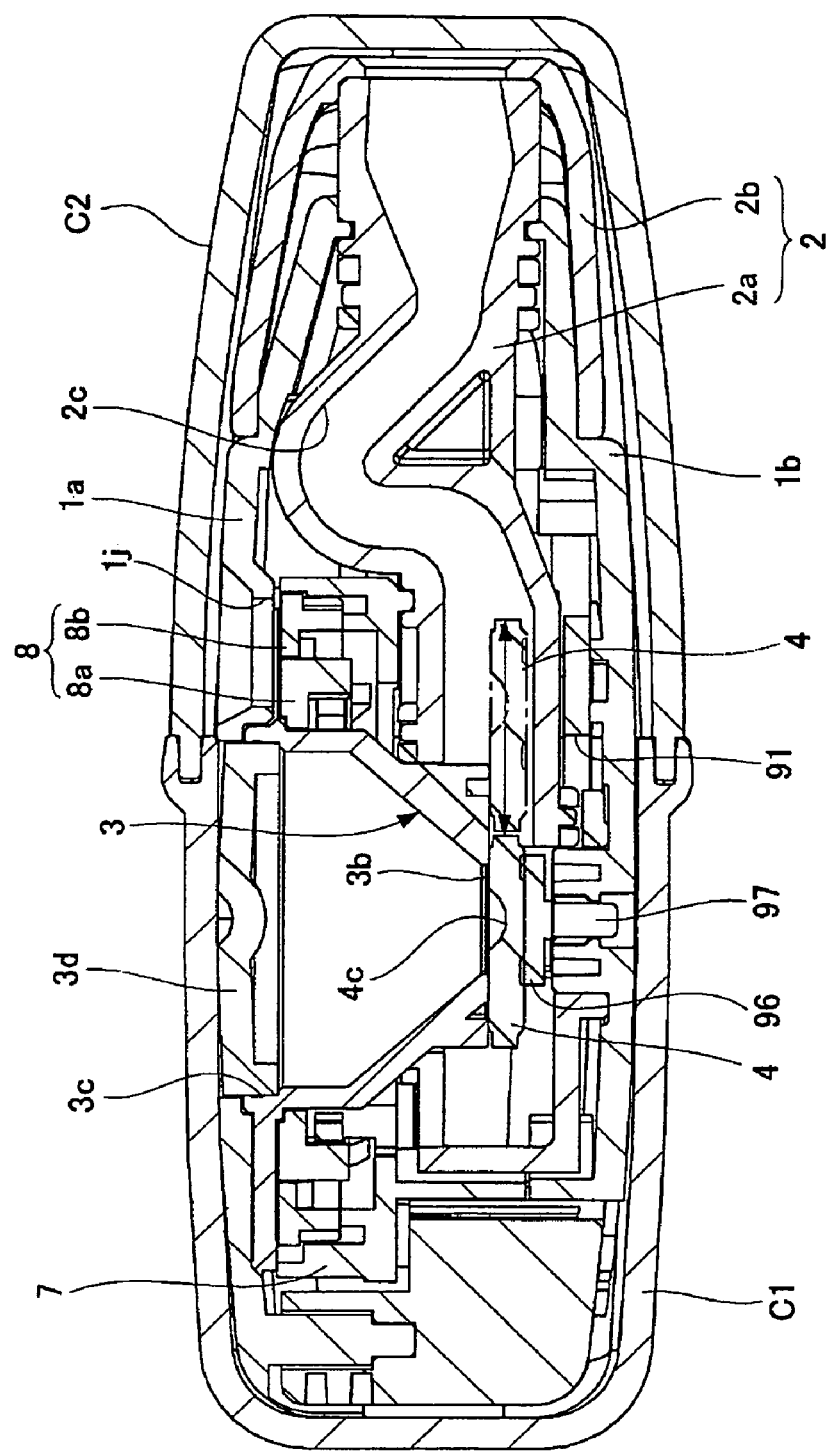
FIG. 26 is an exploded perspective view of the powder inhaler according to the Second Embodiment.
Figure 27:
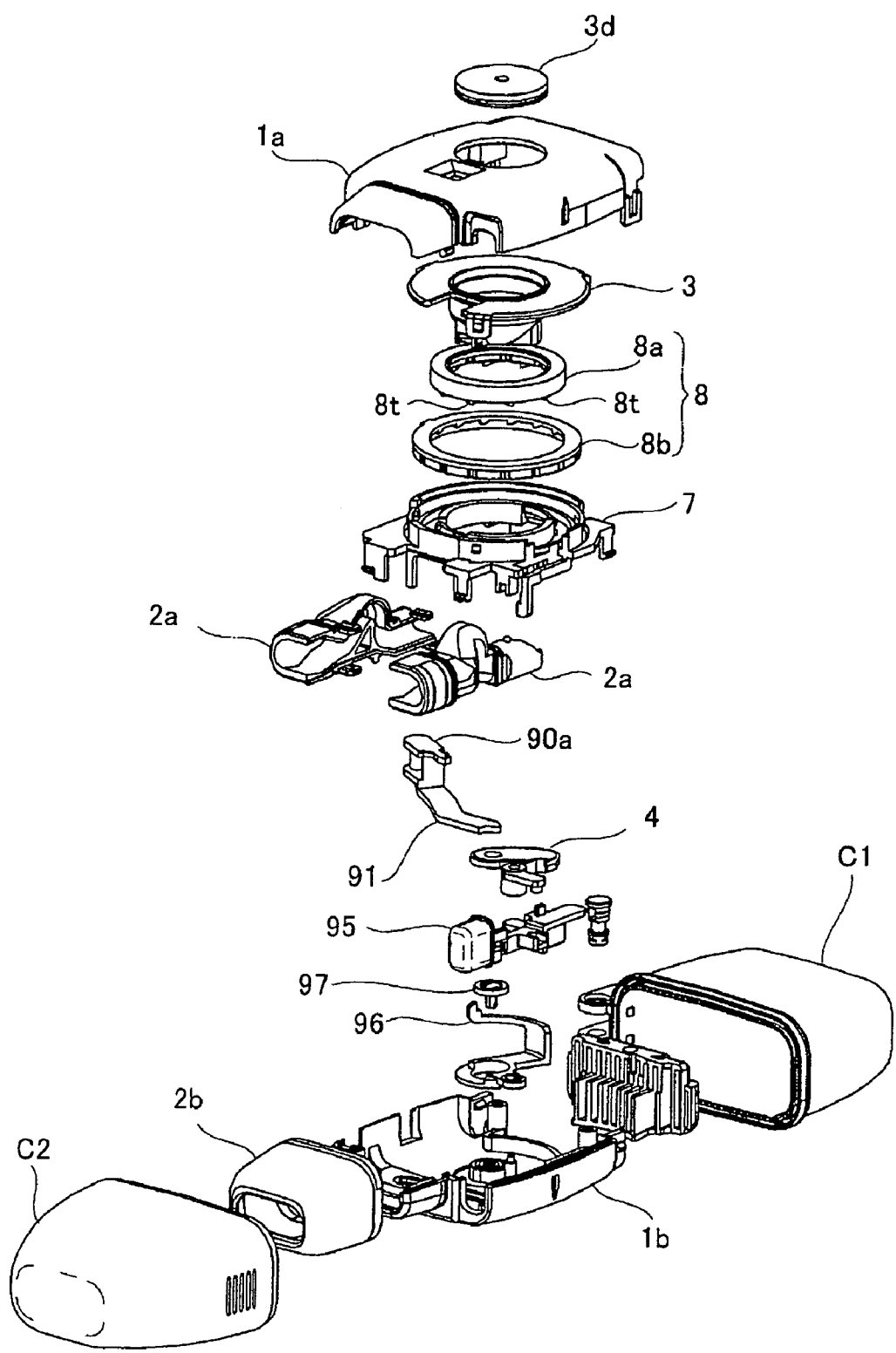
FIG. 27 is a vertical cross-sectional view of the powder inhaler according to the Second Embodiment.
Figure 28:
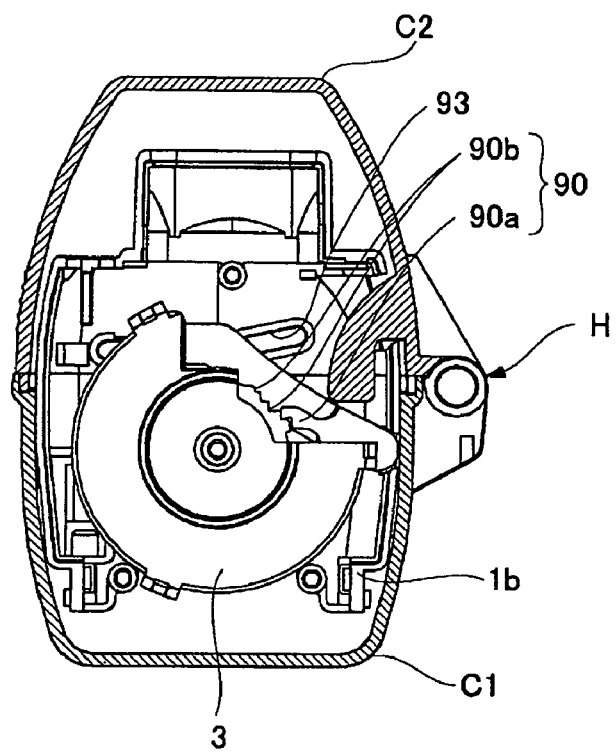
FIG. 28 is a cross-sectional view of an internal structure of the powder inhaler according to the Second Embodiment, for showing a vibrating means of the powder inhaler.
Figure 29:
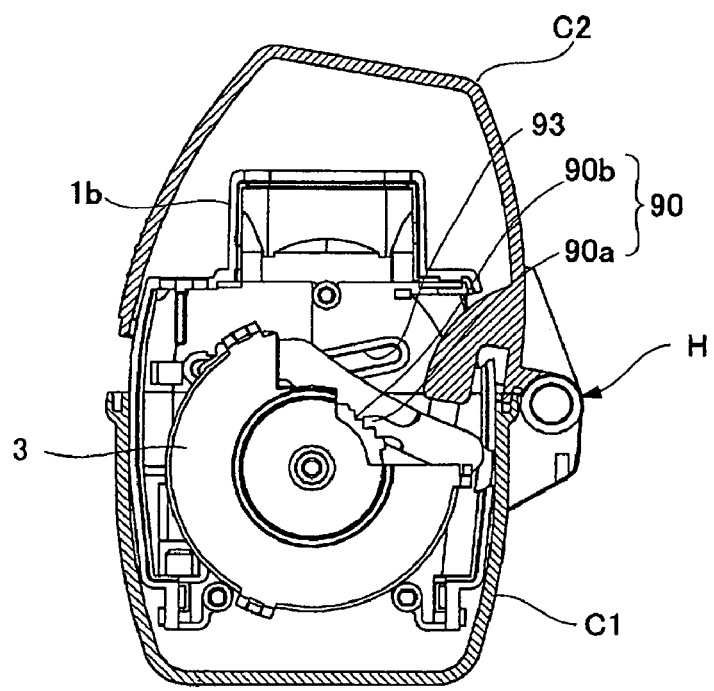
FIG. 29 is a cross-sectional view showing an operation state after FIG. 28.
Figure 30:
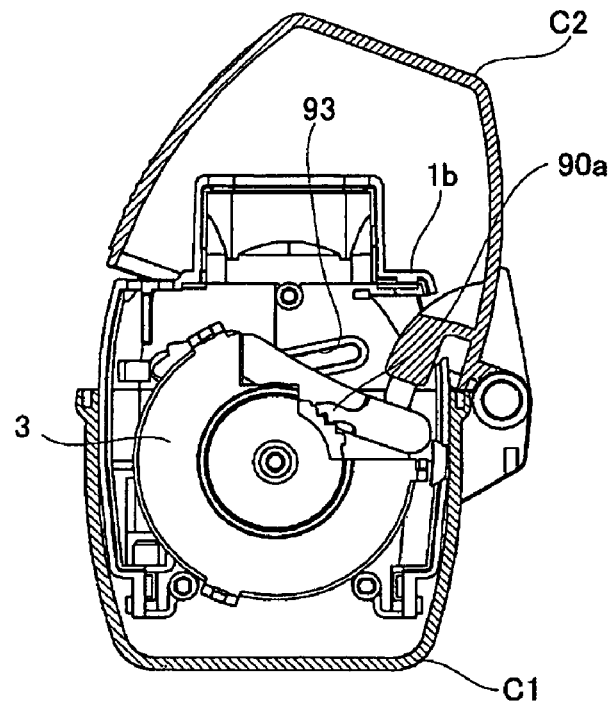
FIG. 30 is a cross-sectional view showing an operation state after FIG. 29.
Figure 31:
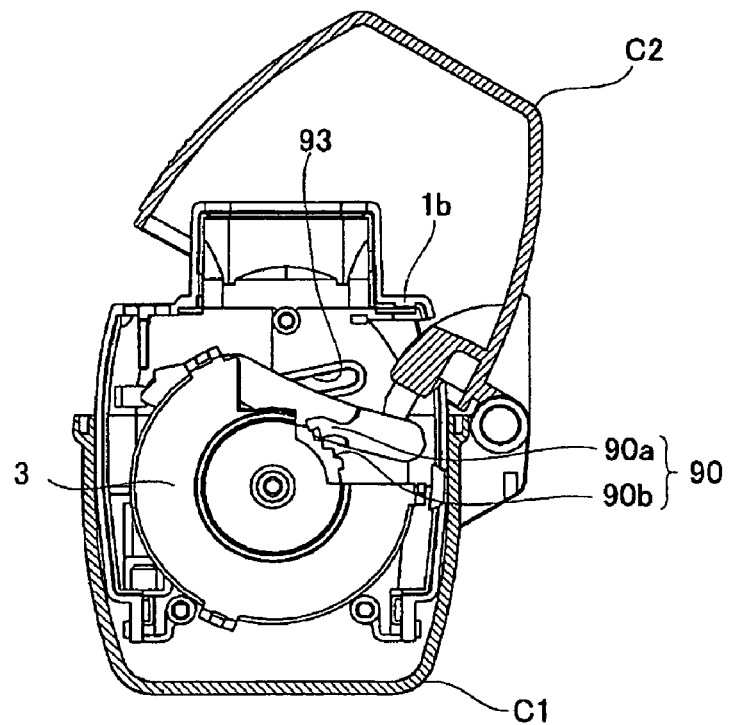
FIG. 31 is a cross-sectional view showing an operation state after FIG. 30.
Figure 32:
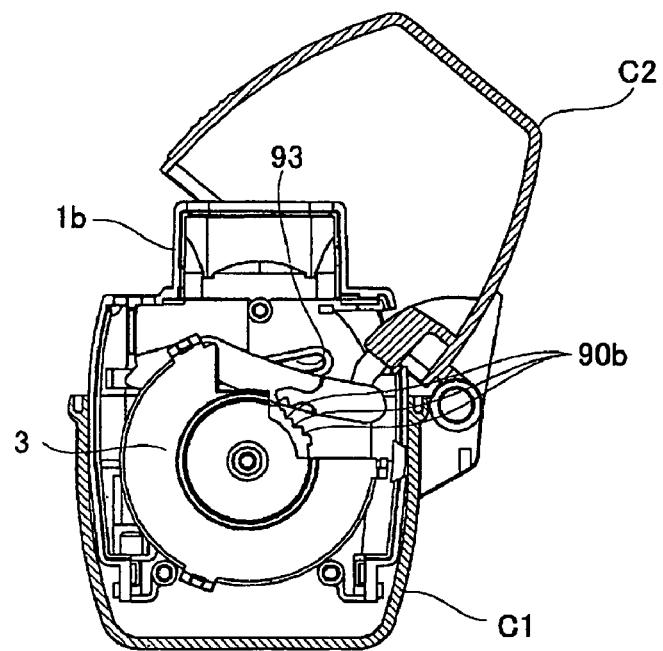
FIG. 32 is a cross-sectional view showing an operation state after FIG. 31.
Figure 33:
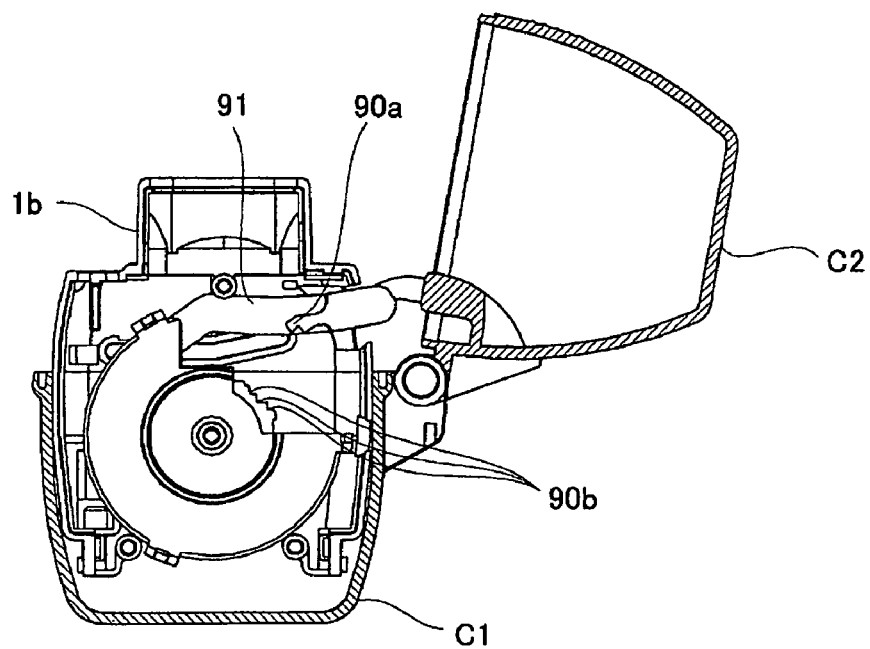
FIG. 33 is a cross-sectional view showing an operation state after FIG. 32.
Figure 34:
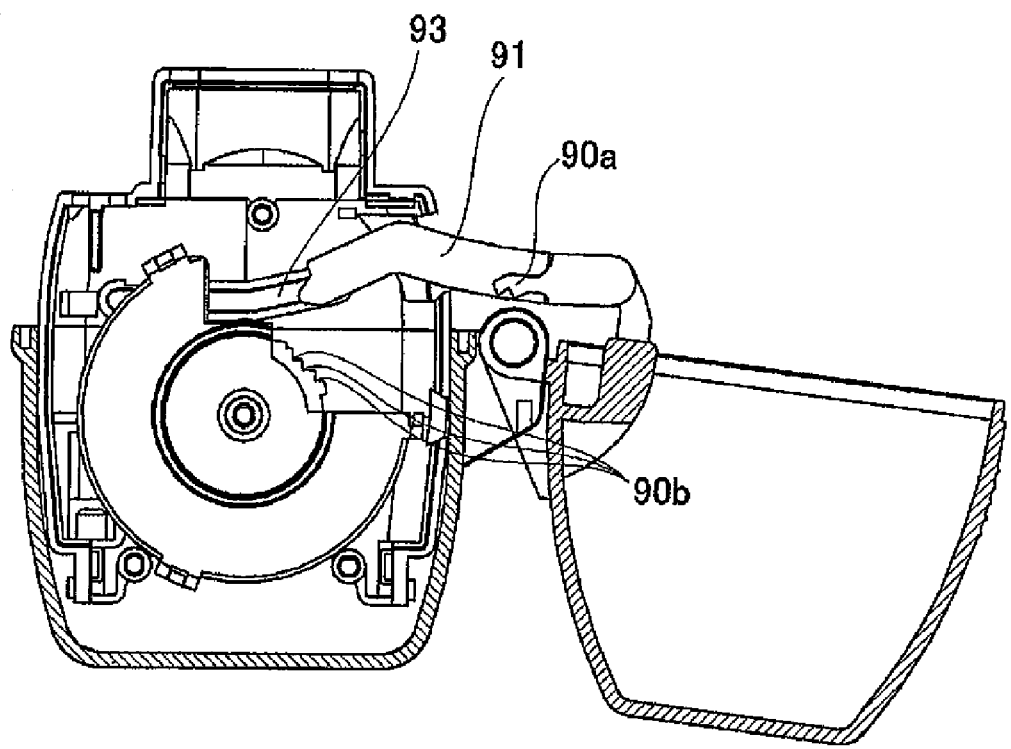
FIG. 34 is a cross-sectional view showing an operation state after FIG. 33.
Figure 35:
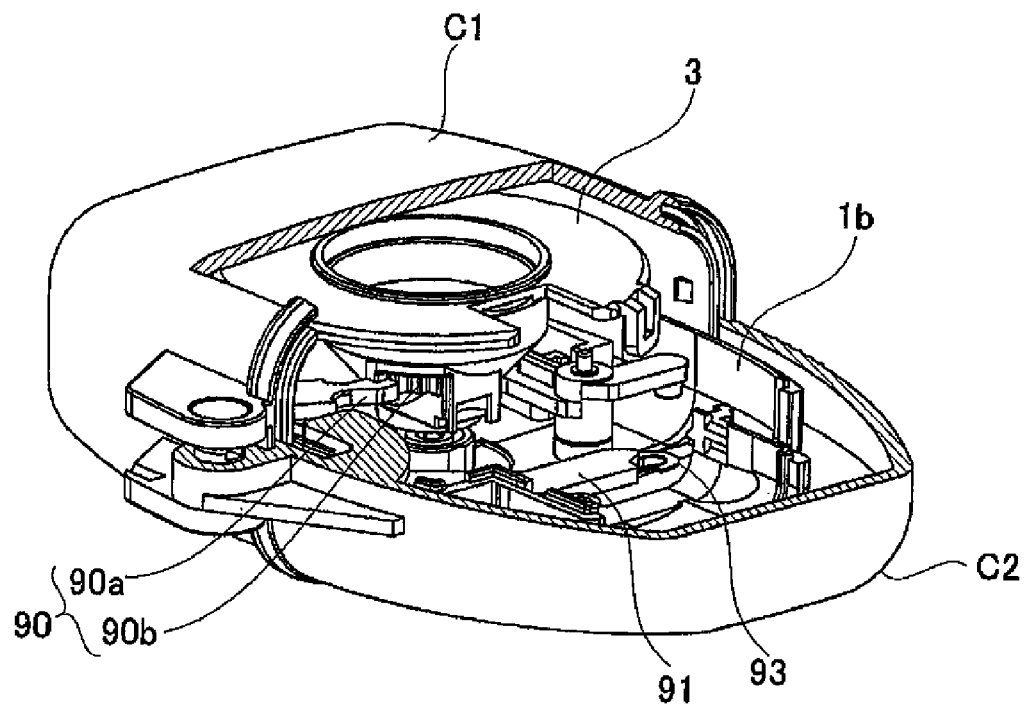
FIG. 35 is a perspective view of a partial internal structure of the powder inhaler according to the Second Embodiment, for showing a vibrating means of the powder inhaler.
Figure 36:
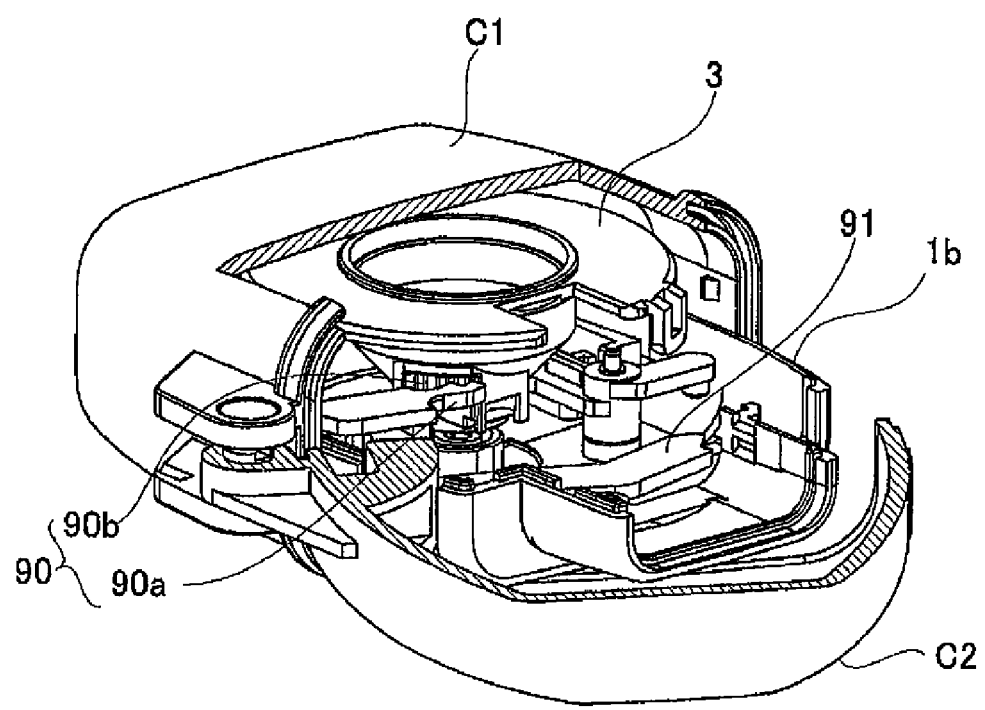
FIG. 36 is a perspective view showing an operation state after FIG. 35.
Figure 37:
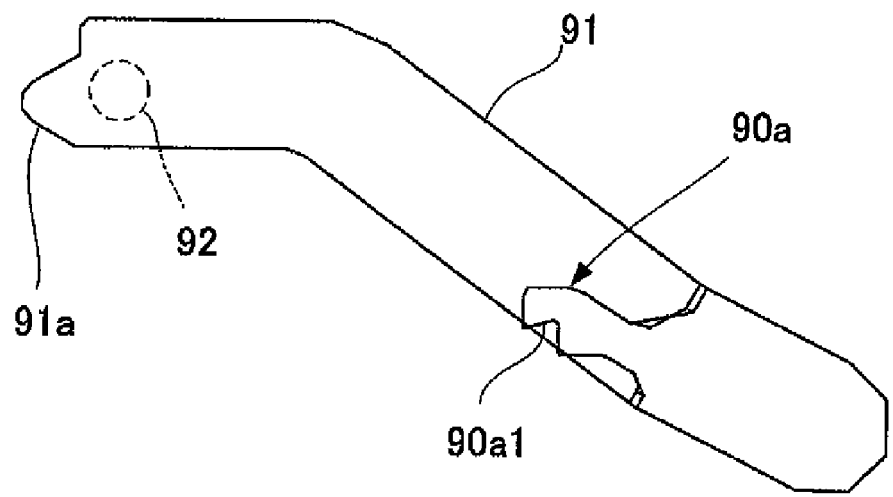
FIGS. 37(a) and 37(b) are a plan view and a lateral view, respectively, of an engagement arm serving as a component of the powder inhaler according to the Second Embodiment.
Figure 37:
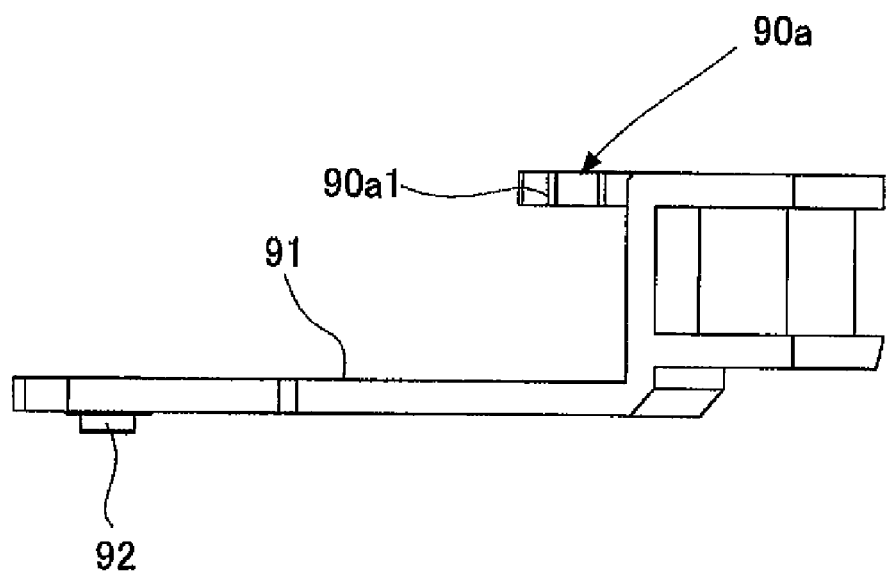

As shown in FIGS. 26 and 27, the housing 1A includes a housing body 1, a mouthpiece 2, and a bottom cap C1 fixed to the housing body 1. The housing 1A contains a supplier 3 for storing multiple doses of a fine powder drug (not shown); a drug carrier 4 for receiving a single dose of the fine powder drug from the supplier 3 to a measurement concave portion 4c and carrying the fine powder drug; a base 7 attached to the housing body 1 via a snap-engagement to hold the supplier 3; and a counter 8 rotatably supported between the supplier 3 and the base 7 and displays the number of doses. The bottom cap C1 covers the housing 1A from the back and is fixed to the housing 1A in a snap-in manner.

The housing body 1 is assembled by connecting an upper housing body 1a and a lower housing body 1b. The mouthpiece 2 is made of a main body 2a and a cover 2b. The main body 2a includes a drug inhalation path 2c for dispersing fine powder. The supplier 3 includes a funnelform hopper 3a for storing about 200 doses of the fine powder drug. A drug discharge outlet 3b is formed on the lower end of the hopper 3a. The opening 3c on the upper end of the hopper 3a of the supplier 3 is closable with a lid 3d to protect the fine powder drug from moisture.

The powder inhaler is brought into operation by pivoting the cover cap C2. The powder inhaler includes a vibrating means 90 that directly vibrates the supplier 3. The vibrating means 90 includes a first engagement section disposed inside the cover cap C2, and a second engagement section disposed in the supplier to be engageable with the first engagement section.

As shown in FIGS. 25, 28 to 34, the first engagement section has an engagement arm 90a pivotably connected to the inside of the cover cap C2. The engagement arm 90a is supported by a bracket C2a fixed to the cover cap C2. As FIGS. 28 to 36 show that portions of the supplier 3a are cut out, the second engagement section engageable with the first engagement section includes a plurality of step portions 90b along the outer lateral face of the funnelform supplier 3. For ease of explanation, FIGS. 28 to 36 omit some components.

The engagement arm 90a includes a guide arm 91 integral with the engagement arm 90a. The guide arm 91 includes a cam follower 92 (see FIG. 37). The cam follower 92 is guided by a guide member 93 formed inside of the housing body 1. The guide member 93 is formed of a standing wall provided on the bottom face of the housing body 1, and functions like a cam groove. As the cover cap C2 is opened, the cam follower 92 is guided by the guide member 93. As a result, as shown in FIGS. 28 to 32, the engagement arm 90a is engaged with one of the step portions 90b, and pushes the supplier 3 as it passes through the irregularities of the step portions 90b, thereby vibrating the supplier 3. Further, when the engagement arm 90a is moved along the step portions 90b, the engagement arm 90a collides with the irregularities of the step portions 90b. This also causes vibration of the supplier 3. The engagement arm 90a includes a cut-out portion 90a1 on its top end. The cut-out portion 90a1 is engaged with the step portions 90b. When the cover cap C2 is closed, the engagement arm 90a travels inversely to when the cover cap C2 is opened.

The housing body 1 includes an opening 1c to let the guide arm 91 and engagement arm 90a through. As shown in FIG.

26, the guide arm 91 extends between the main body 2a of the mouthpiece 2 and the housing body 1.

As described, the bottom cap C1 of the Second Embodiment differs from that of the First Embodiment in that it is fixed to the housing body 1. Therefore, in the Second Embodiment, as shown in FIG. 25, an operating member 95 that moves the drug carrier 4 from the drug-receiving position to the drug-inhalation position is projected from the front shoulder of the housing body 1 to serve as a push-button. In FIGS. 28 to 36, the operating member is omitted.

Figure 38:
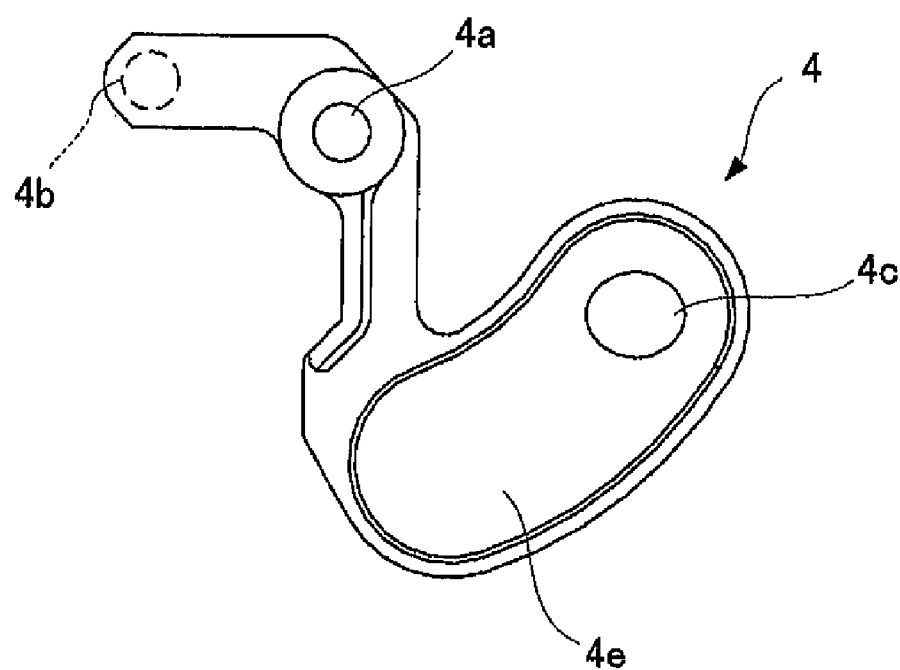
FIGS. 38(a) and 38(b) are a plan view and a lateral view, respectively, of a drug carrier of the powder inhaler according to the Second Embodiment.
Figure 38:
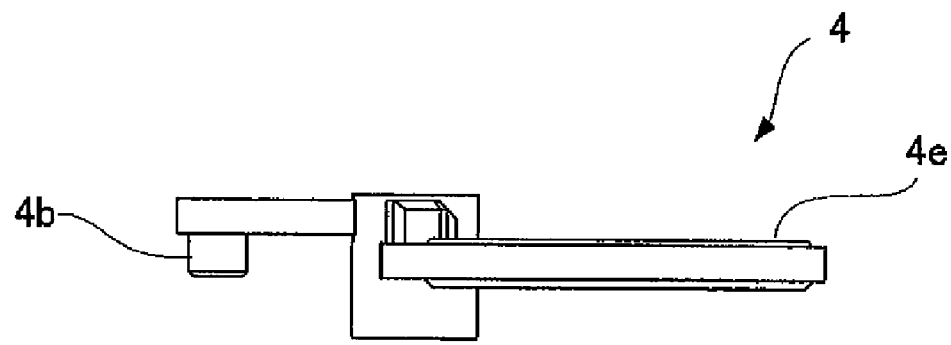
Figure 39:
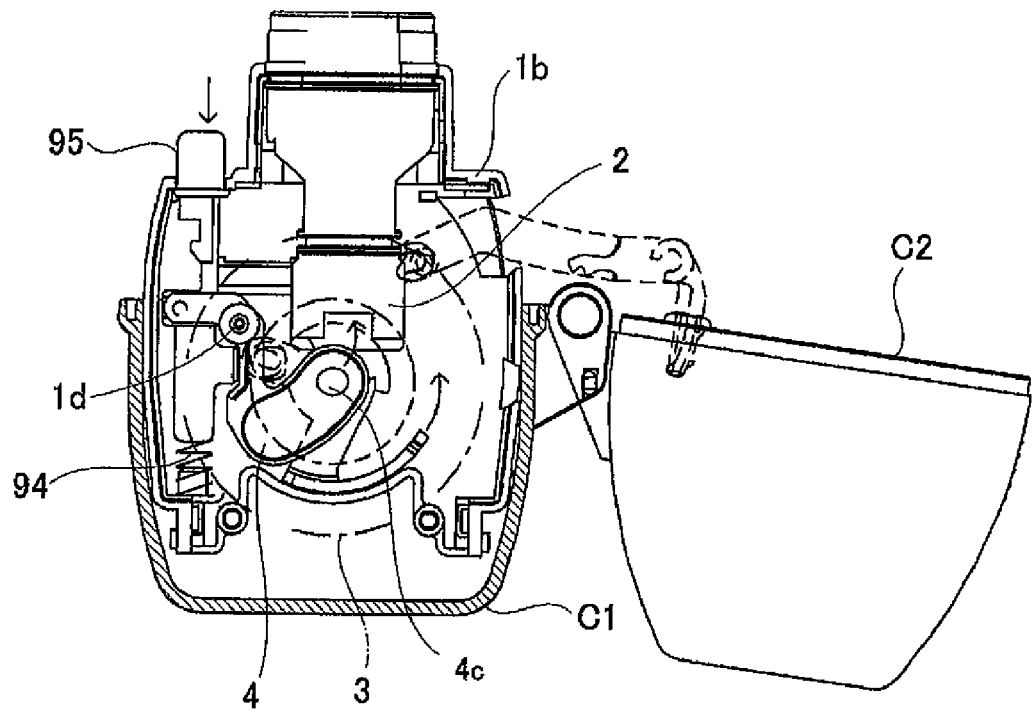
FIG. 39 is a cross-sectional view of an internal structure of the powder inhaler according to the Second Embodiment, for showing an operation state of the drug carrier.
Figure 40:
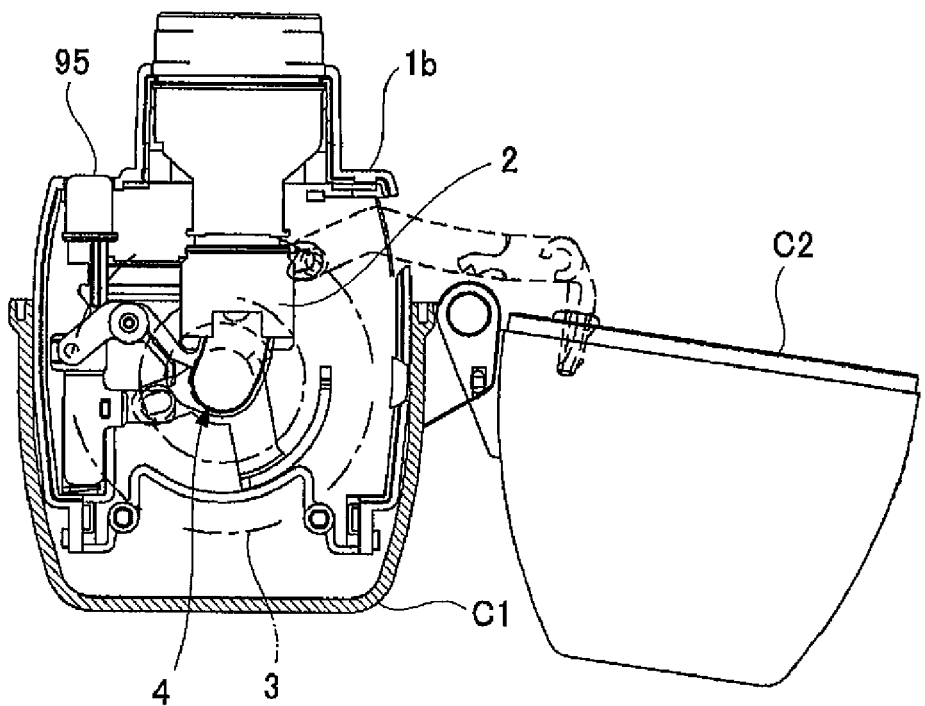
FIG. 40 is a cross-sectional view showing operation state after FIG. 39.

As shown in FIG. 38, the drug carrier 4 includes an axis hole 4a, a latching pin 4b, a measurement concave portion 4c, and a sliding portion 4e. As shown in FIGS. 39 and 40, the drug carrier 4 is rotatably supported by an axis 1d projected from the housing body 1.

The latching pin 4b of the drug carrier 4 is supported by an axis-receiving portion 95a (see FIG. 43) formed on the operating member 95. As shown in FIG. 39, the operating member 95 is biased by an elastic member 94 made of a coil spring or the like to be projected from the housing body 1. When the operating member 95 is not pressed against the elastic member 94, as shown in FIG. 39, the drug carrier 4 is disposed by the elastic member 94 in the drug-receiving position where the measurement concave portion 4c is connected to a drug-discharging hole (not shown in FIG. 39). When the operating member 95 is pressed against the elastic member 94, as shown in FIG. 40, the drug carrier 4 is pivoted around the axis 1d, and the measurement concave portion 4c moves to the drug-inhalation position in the mouthpiece 2.

Figure 41:
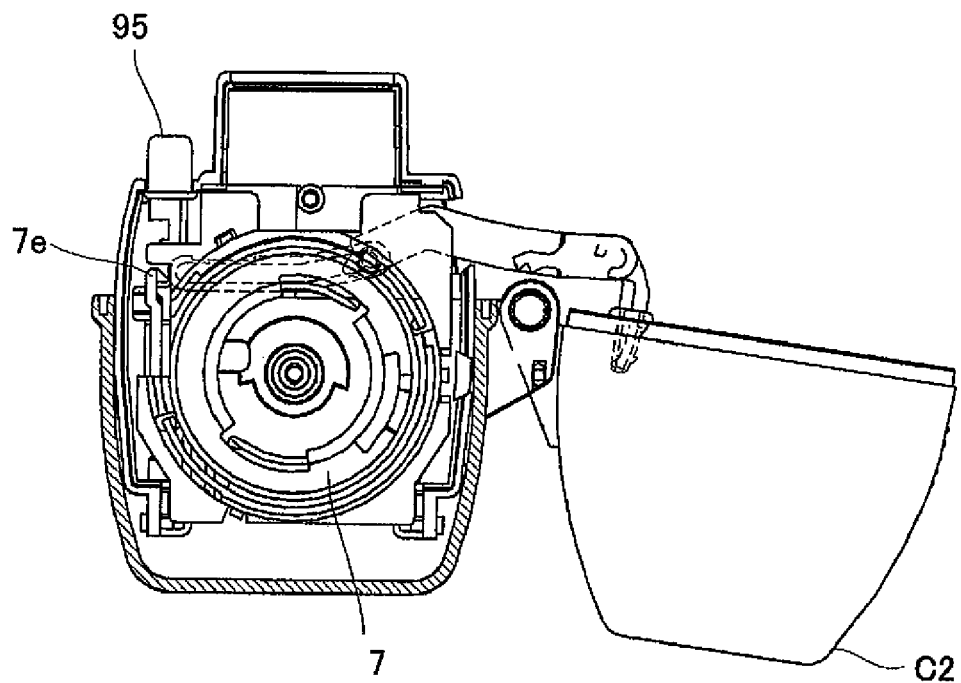
FIG. 41 is a cross-sectional view of an internal structure of the powder inhaler according to the Second Embodiment, for showing a lock mechanism of the powder inhaler.
Figure 42:
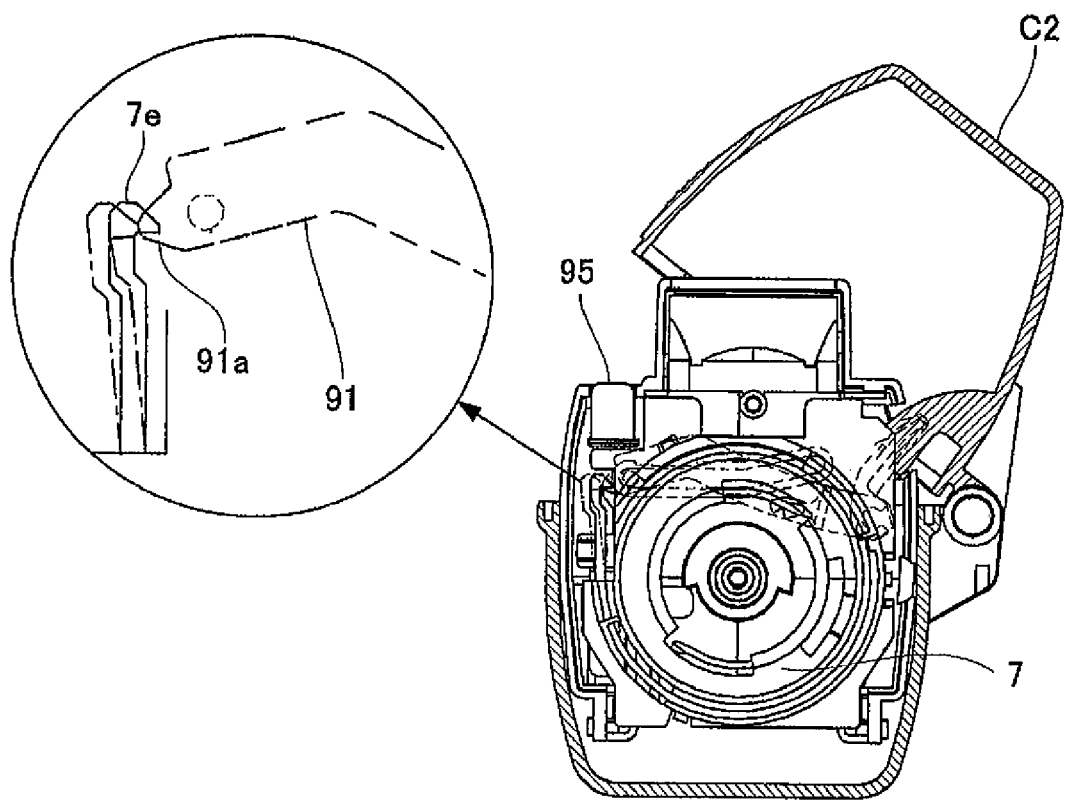
FIG. 42 is a cross-sectional view of an internal structure of the powder inhaler according to the Second Embodiment, for showing a lock-releasing mechanism of the powder inhaler.
Figure 43:
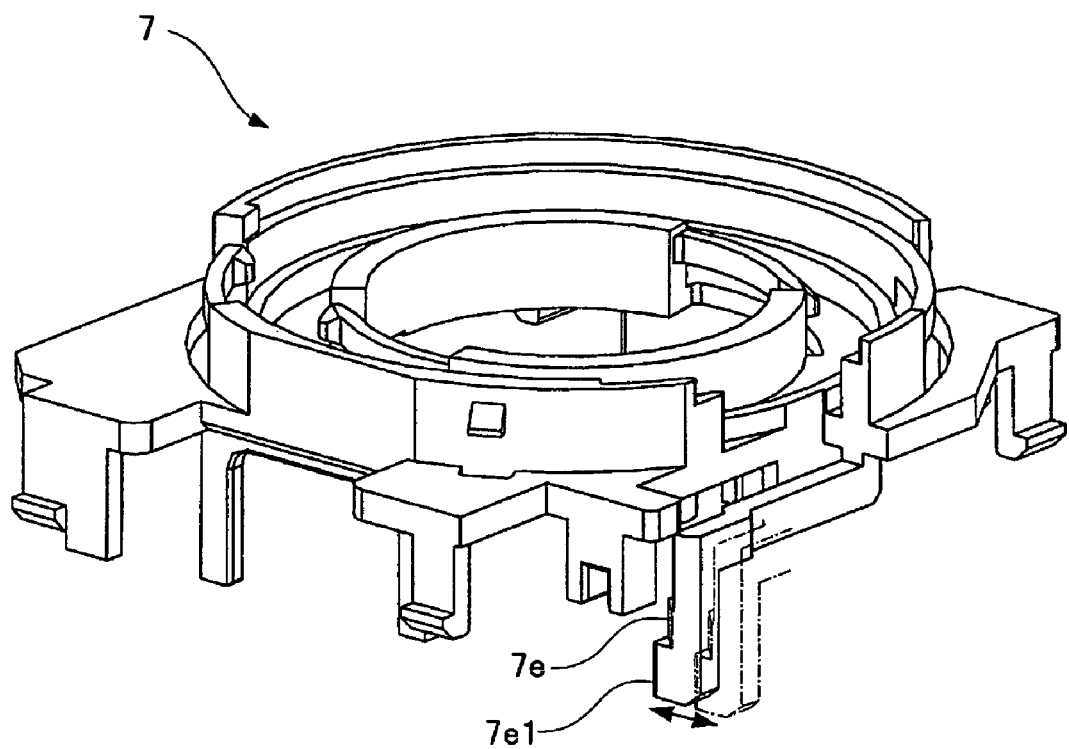
FIG. 43 is a perspective view of a base and an operating member incorporated in the powder inhaler according to the Second Embodiment.
Figure 43:
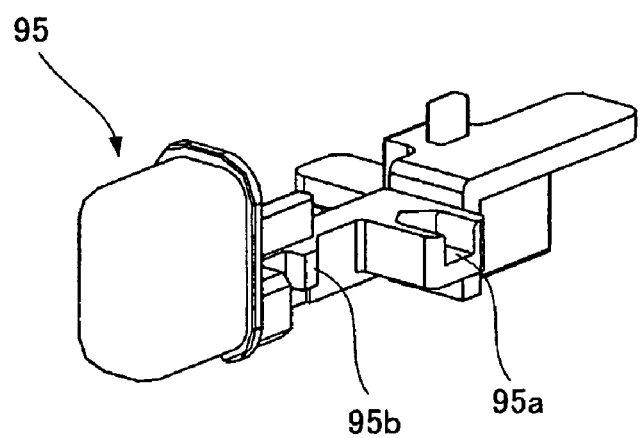

When the operating member 95 is pushed inward, which moves the drug carrier 4 to the drug-inhalation position, the lock mechanism is activated by the elastic force of the elastic member 94 to restrict the movement of the drug carrier 4 toward the drug-receiving position. As shown in FIGS. 41 to 43, the lock mechanism includes a latching arm 7e extending from the base 7, and a latching pawl 95b formed on the operating member 95. More specifically, by pushing the operating member 95, the latching pawl 95b is latched with the latching arm 7e, thereby activating the lock mechanism.

A lock-releasing member serving as a lock-releasing mechanism of the lock mechanism is provided on the front end 91a of the guide arm 91 in FIG. 42. As shown therein, when the cover cap C2 is closed, the guide arm 91 is guided by the guide member 93, which causes the front end 91a of the guide arm 91 to push the front end 7e1 of the latching arm 7e (see FIG. 43). As a result, as shown in FIGS. 42 and 43, the latching arm 7e bends, and is thereby disengaged from the latching pawl 95b. This disengagement of the latching arm 7e from the latching pawl 95b immediately causes the elastic member 94 to push back the operating member 95. As a result, the drug carrier 4 moves from the drug-inhalation position to the drug-receiving position.

The following briefly explains the counter 8 (see FIG. 27). As in the First Embodiment, the counter 8 has a structure according to a known art.

Figure 44:
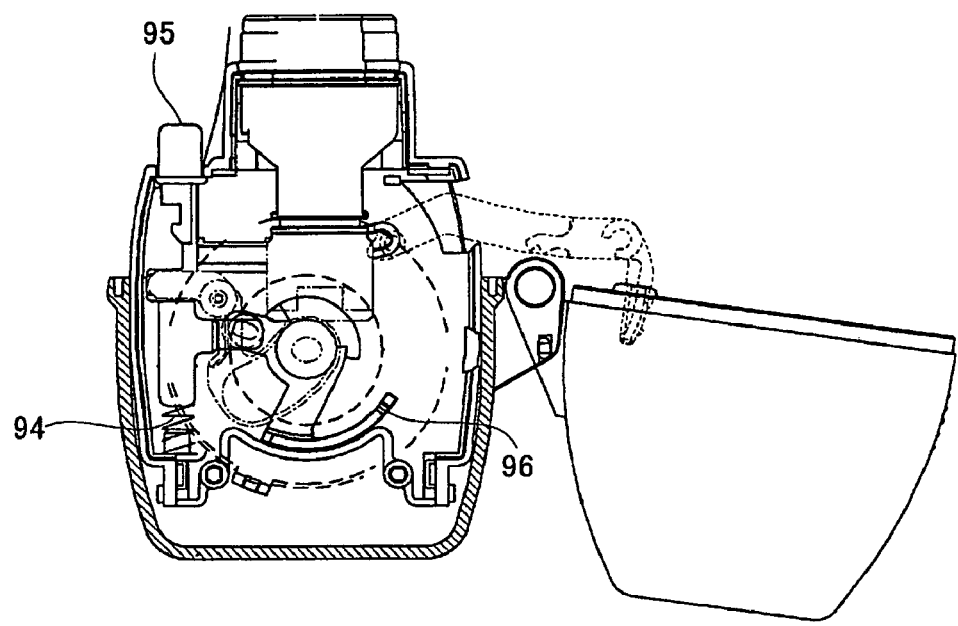
FIG. 44 is a cross-sectional view of an internal structure of the powder inhaler according to the Second Embodiment, for showing a counter of the powder inhaler.
Figure 45:
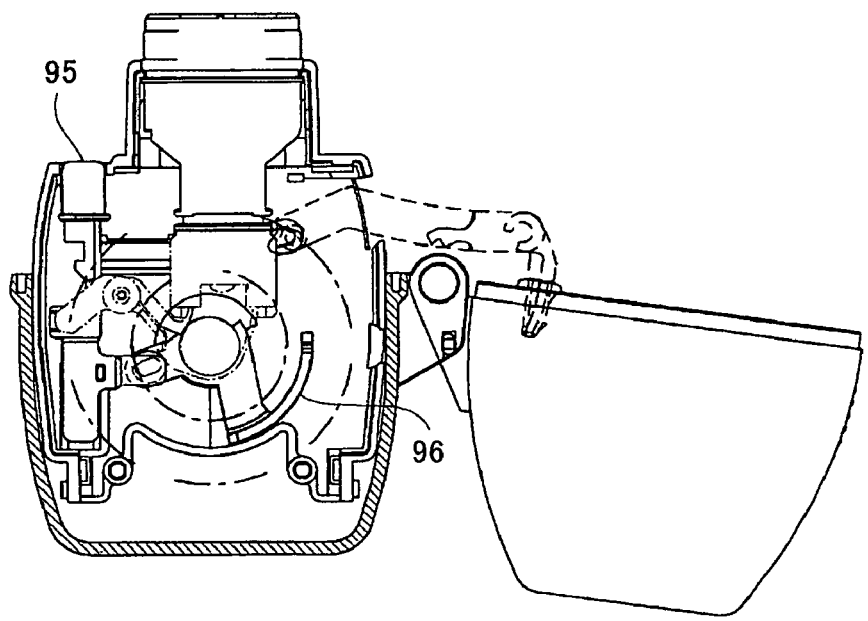
FIG. 45 is a cross-sectional view showing an operation step after FIG. 44.
Figure 46:
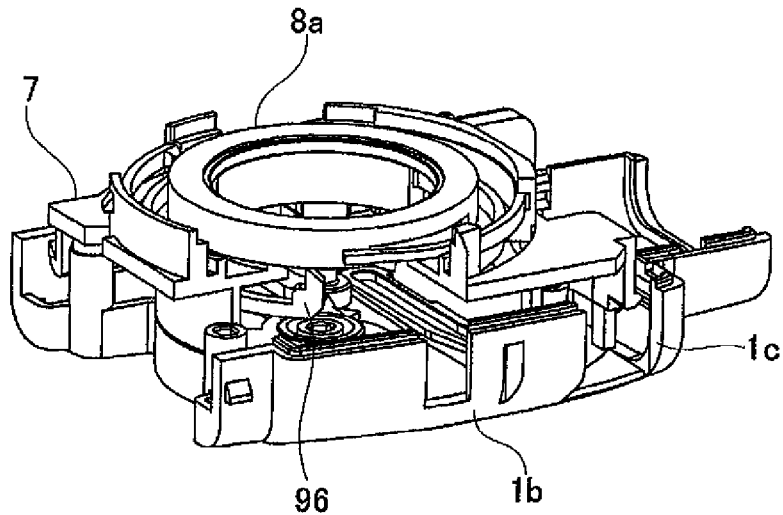
FIG. 46 is a perspective view of a partial internal structure of the powder inhaler according to the Second Embodiment, for showing a counter of the powder inhaler.

As shown in FIGS. 44 and 45, the ratchet-driving pawl 96 for driving the circular ring 8a, which denotes a unit's place of the counter is supported in the housing body 1. The ratchet-driving pawl is connected with the operating member 95 by a link connection so that it is pivoted around the axis 97 (see FIGS. 26 and 27) by the operating member 95.

Figure 47:
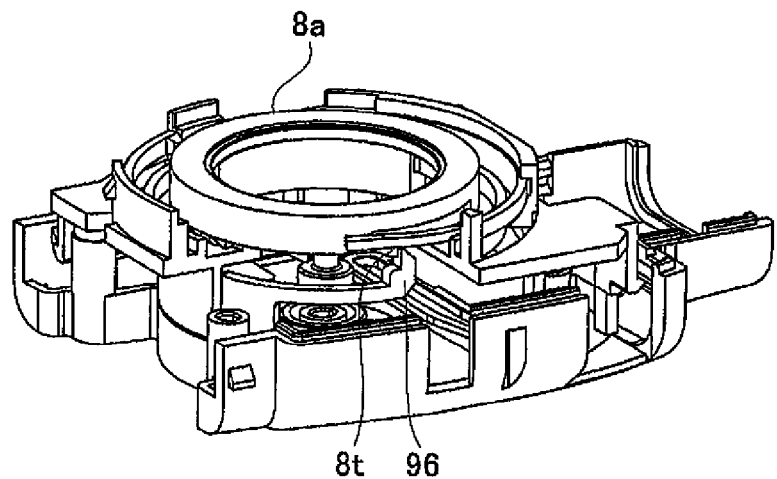
FIG. 47 is a perspective view showing an operation state after FIG. 46.
Figure 48:
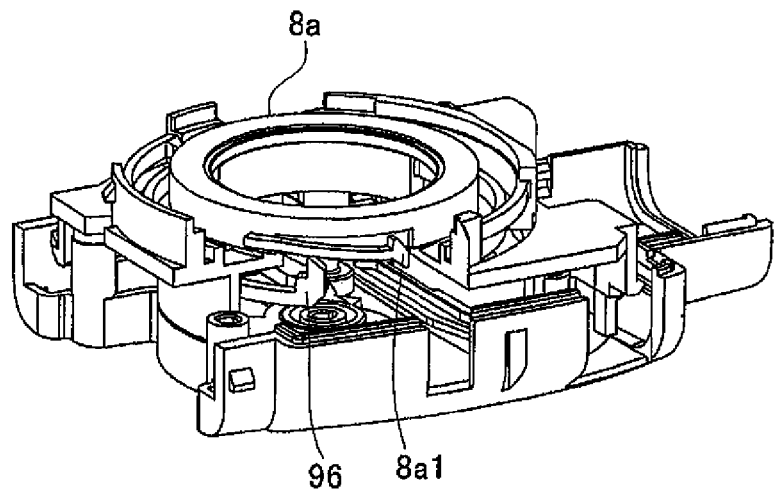
FIG. 48 is a perspective view showing an operation state after FIG. 47.

Once the operating member 95 is pressed, the ratchet-driving pawl 96 moves from the position shown in FIG. 44 (FIG. 46) to the position shown in FIG. 45 (FIG. 47). As shown in FIG. 47, the ratchet-driving pawl 96 is latched with the latchet tooth 8t formed on the bottom of the circular ring 8a. Subsequently, the lock mechanism is unlocked by the lock-releasing member, and the operating member 95 returns to the position shown in FIG. 44, from the position shown in FIG. 45. With this movement of the operating member 95, the ratchet-driving pawl 96 moves from the position shown in FIG. 47 to the position shown in FIG. 48 to rotate the circular ring 8a denoting a unit's place. When the circular ring 8a denoting a unit's place completed a revolution after the user pressed the operating member 95 ten times, the ratchet-driving pawl 8a1 is engaged with an annulus ring 8b denoting a ten's place (FIG. 27), thereby rotating the annulus ring 8b. The number in the counter 8 can be seen through the window 1j (see FIG. 25) provided in the housing body 1.

Figure 49:
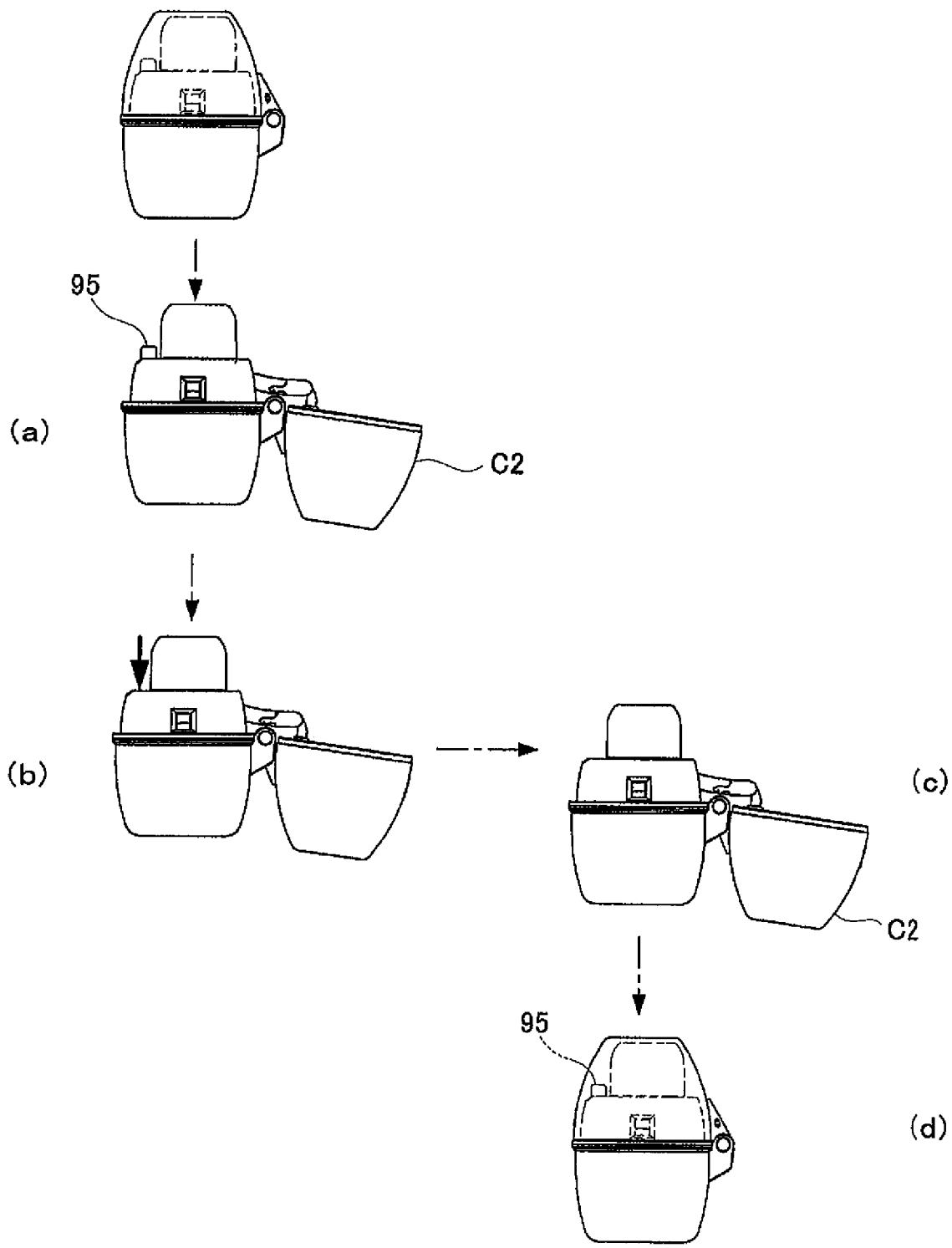
FIG. 49 is an explanatory view showing operation steps of the powder inhaler according to the Second Embodiment.

As shown in FIG. 49, the powder inhaler according to the Second Embodiment enables the user to complete inhalation in the following four steps.

(a) opening the cover cap C2;
(b) pressing the operating member 95;
(c) inhaling; and
(d) closing the cover cap C2.

More specifically, with the opening movement of the cover cap C2, the vibrating means 90 vibrates the supplier 3, thereby causing the supplier 3 to fill the measurement concave portion 4c with the fine powder drug. This spares the user the effort of holding and shaking the powder inhaler by hand.

After inhalation, the lock-releasing member unlocks the lock mechanism as the cover cap C2 is closed, thereby moving the drug carrier from the drug-inhalation position back to the drug-receiving position. This spares the user the effort of returning the drug carrier 4 to the drug-receiving position.

The embodiments and specific examples of implementation discussed in the foregoing detailed explanation serve solely to illustrate the technical details of the present invention, which should not be narrowly interpreted within the limits of such embodiments and concrete examples, but rather may be applied in many variations, provided such variations do not exceed the scope of the present invention.

For example, the second engagement section is formed in the outer lateral face of the housing body 1 in the First Embodiment; however, as in the Second Embodiment, the second engagement section may be so formed as to extend inside the housing 1A so as to reside in the housing body 1.

Figure 50:
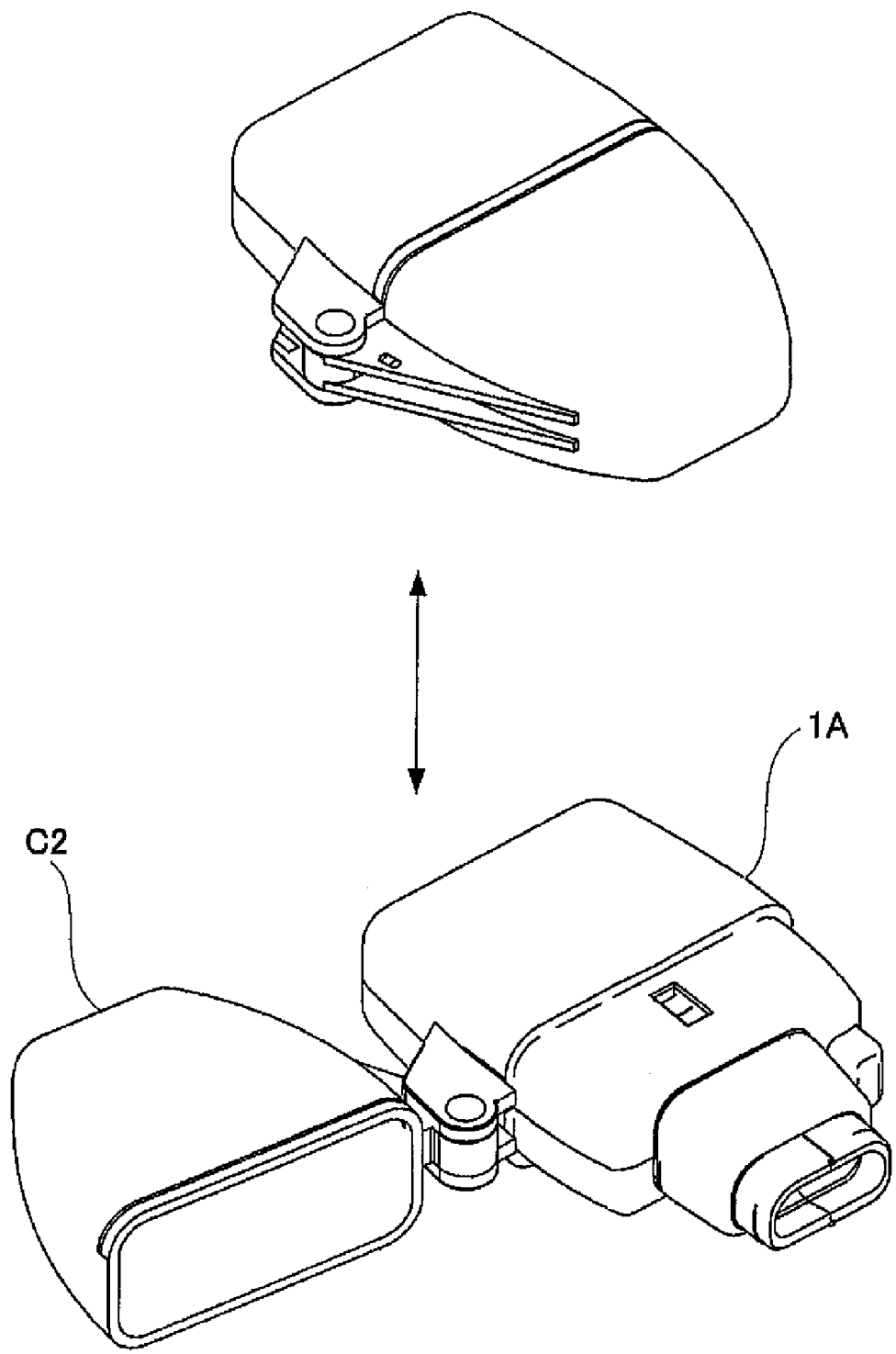
FIG. 50 is a perspective view of a modification of the powder inhaler according to the Second Embodiment.

Further, although the Second Embodiment describes that the housing 1A is formed by attaching the bottom cap C1 to the housing body 1, as shown in FIG. 50, bottom cap C1 may be omitted by forming a bottom portion in the component corresponding to the housing body 1. In this case, the separate bottom cap is not required.

Furthermore, in the foregoing embodiments, the second engagement section is formed in the housing body or on a supplier to serve as a vibrating means that is engaged with the first engagement section formed on the cover cap C2; however, the second engagement section may be formed on any members that can transmit the vibration to the supplier, for example, on the base 7 for supporting the supplier 3, or on the other built-in components of the housing 1A.

Figure 51:
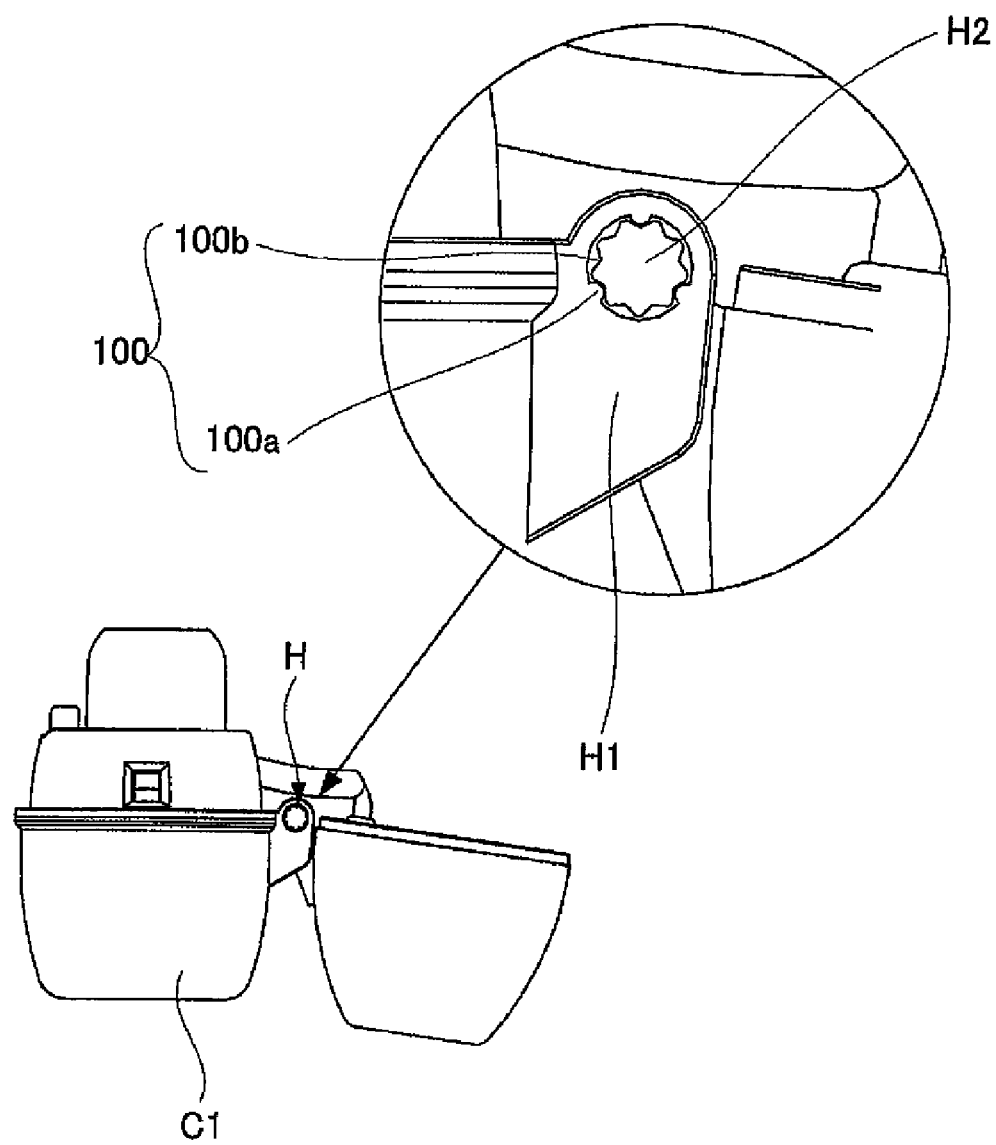
FIG. 51 is a magnified plan view showing a part of another modification of a powder inhaler according to the present invention.
Figure 52:
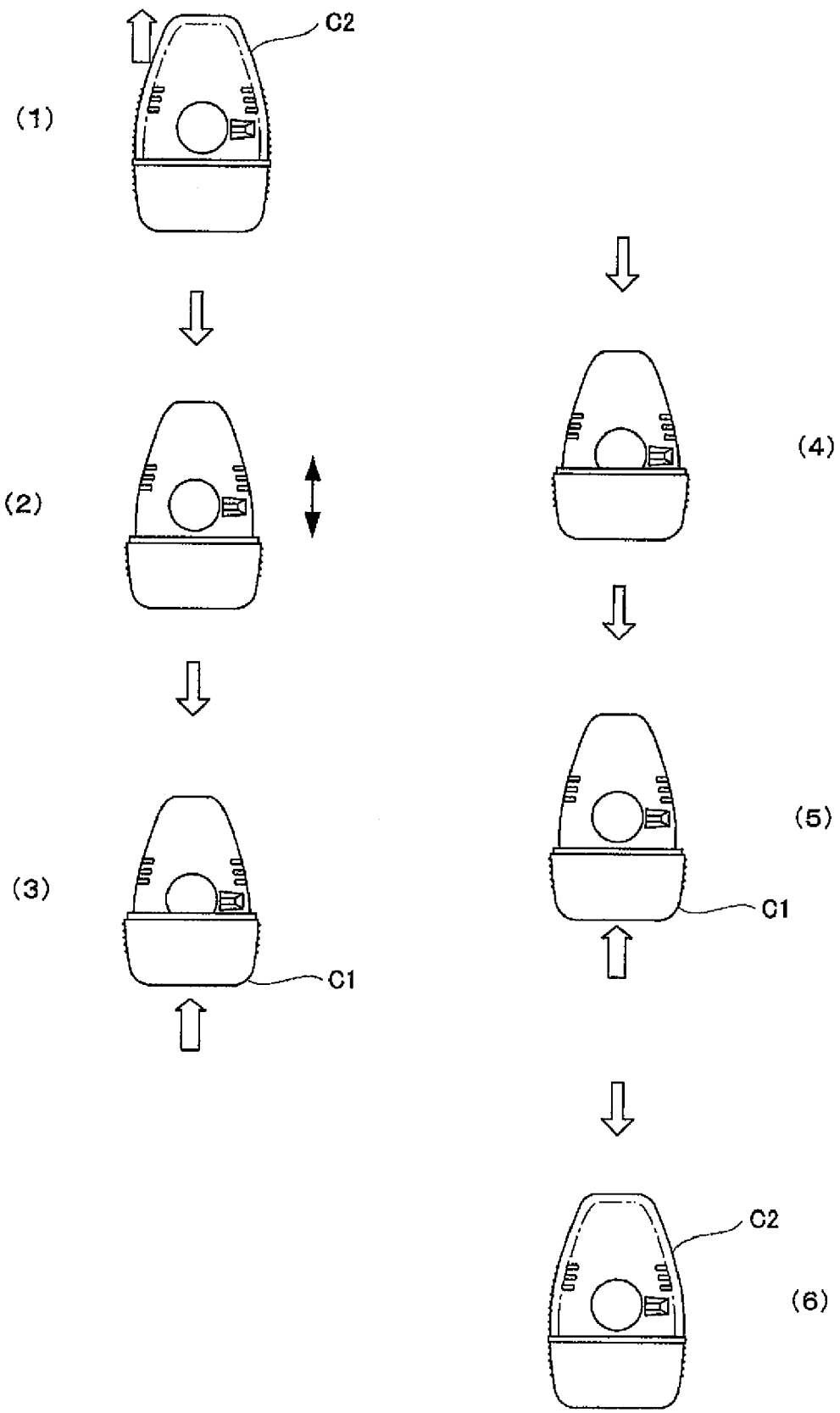
FIG. 52 is an explanatory view showing operation steps of an existing powder inhaler.

The second engagement section serving as a vibrating means is not limited to the built-in component of the housing, and may be provided on, for example, a portion integrated with the housing 1A, as long as it is engageable with the first engagement section while transmitting vibration to the supplier. For example, as shown in FIG. 51, the second engagement section serving as the vibrating means 100 and engaged with the first engagement section may be realized by a projection portion 100a provided on the inner periphery of the axis-receiving portion H1 of the hinge H that is integrated with the bottom cap C1 constituting the housing 1A. In this case, the first engagement section provided on the cover cap C2 may be realized by a convex/concave portion 100b provided on the outer periphery of the axis member H2 of hinge H, instead of the one inside the cover cap.

The invention claimed is:

1. A powder inhaler, comprising:
   a housing having an admission port on one end;
   a supplier having a drug-discharging hole, provided inside the housing with a capacity sufficient to contain plural doses of a fine powder drug;
   a drug carrier having a measurement concave portion for receiving a single dose of the drug from the drug-discharging hole, the drug carrier being supported inside the housing while being movable between a drug-receiving position for allowing drug supply from the drug-discharging hole to the measurement concave portion, and a drug-inhalation position for allowing drug inhalation from the measurement concave portion through the admission port;
   a cover cap pivotably mounted to the housing;
   at least one first engagement section formed on the cover cap; and
   at least one second engagement section formed on the housing to transmit vibration to the supplier, and that is engaged with the first engagement section by pivoting the cover cap and thereby vibrating the supplier,
   wherein the supplier and the drug carrier are arranged such that the vibration transmitted to the supplier makes the fine powder drug travel from the supplier to the measurement concave portion; and
   the first engagement section and the second engagement section each have at least one convex portion, the supplier vibrates as a result of moving the convex portions in contact with each other.

2. A powder inhaler according to claim 1, wherein the first engagement section is provided on an inner side of the cover cap.

3. A powder inhaler according to claim 1, wherein the first engagement section is provided on an inner side of the cover cap, and the second engagement section is provided on an external lateral face of the housing.

4. A powder inhaler according to claim 3, wherein the first engagement section is pivotably connected to the inner side of the cover cap, and the housing includes a guide member for pivoting the first engagement section while pivoting the cover cap, and guiding the first engagement section to the second engagement section.

5. A powder inhaler according to claim 1, further comprising:
   an elastic member provided in the housing, to bias the drug carrier from the drug-inhalation position to the drug-receiving position;
   a lock mechanism for locking the drug carrier in the drug inhalation position; and
   a lock-releasing mechanism for unlocking the lock mechanism in response to a closing movement of the cover cap.

6. A powder inhaler according to claim 4, further comprising:
   an elastic member provided in the housing, to bias the drug carrier from the drug-inhalation position to the drug-receiving position;
   a lock mechanism for locking the drug carrier in the drug-inhalation position; and
   a lock-releasing mechanism for unlocking the lock mechanism in response to a closing movement of the cover cap,
   wherein:
   the lock-releasing mechanism includes a lock-releasing member, which is connected to the first engagement section and is guided by a guide section to a lock-releasing position.

7. A powder inhaler according to claim 1, the second engagement section is mounted to a component incorporated in the housing, wherein the component can transmit vibration to the supplier.

8. A powder inhaler, comprising:
   a housing having an admission port on one end;
   a supplier having a drug-discharging hole, provided inside the housing with a capacity sufficient to contain plural doses of a fine powder drug;
   a drug carrier having a measurement concave portion for receiving a single dose of the drug from the drug-discharging hole, the drug carrier being supported inside the housing while being movable between a drug-receiving position for allowing drug supply from the drug-discharging hole to the measurement concave portion, and a drug-inhalation position for allowing drug inhalation from the measurement concave portion through the admission port;
   a cover cap pivotably mounted to the housing; and
   a vibrating means brought into operation by pivoting the cover cap so as to vibrate the supplier,
   wherein the supplier and the drug carrier are arranged such that the vibration of the supplier makes the fine powder drug travel from the supplier toward the measurement concave portion; and
   the vibrating means has at least one pair of convex portions, the supplier vibrates as a result of moving the convex portions, in contact with each other.

9. A powder inhaler according to claim 8, wherein the vibrating means includes at least one first engagement section mounted to the cover cap; and at least one second engagement section provided on the housing, and that is engaged with the first engagement section.

10. A powder inhaler according to claim 8, wherein the vibrating means includes at least one first engagement section mounted to the cover cap; and at least one second engagement section provided on the supplier, and that is engaged with the first engagement section.

* * * * *